(12) United States Patent
Shinohara

(10) Patent No.: US 8,709,794 B2
(45) Date of Patent: Apr. 29, 2014

(54) METHOD FOR PRODUCING CARRIER ON WHICH MICROORGANISMS CAPABLE OF CONDUCTING MULTIPLE PARALLEL MINERALIZATION ARE IMMOBILIZED, COLUMN REACTOR AND SOLID MEDIUM FOR CULTIVATING PLANTS

(75) Inventor: Makoto Shinohara, Tsu (JP)

(73) Assignee: Makoto Shinohara, Tsu-shi, Mie (JP)

( * ) Notice: Subject to any disclaimer, the term of this patent is extended or adjusted under 35 U.S.C. 154(b) by 432 days.

(21) Appl. No.: 13/056,117

(22) PCT Filed: Jul. 16, 2009

(86) PCT No.: PCT/JP2009/062868
§ 371 (c)(1),
(2), (4) Date: Jan. 26, 2011

(87) PCT Pub. No.: WO2010/041502
PCT Pub. Date: Apr. 15, 2010

(65) Prior Publication Data
US 2011/0126457 A1 Jun. 2, 2011

(30) Foreign Application Priority Data
Oct. 9, 2008 (JP) ................................. 2008-262385

(51) Int. Cl.
*C12M 1/00* (2006.01)
(52) U.S. Cl.
USPC ...................................................... 435/290.1
(58) Field of Classification Search
USPC ......... 47/59 S, 58.1 R, 1.4; 71/11–26, 6, 7, 8, 71/9, 10; 435/290.1, 290.2, 290.3, 290.4; 423/394, 351, 385, 395
See application file for complete search history.

(56) References Cited

U.S. PATENT DOCUMENTS 3,250,606 A * 5/1966 Murray ............................. 71/1
4,009,099 A * 2/1977 Jeris ............................... 210/612
(Continued)

FOREIGN PATENT DOCUMENTS

JP 6-125668 A 5/1994
JP 2001-300583 A 10/2001
(Continued)

OTHER PUBLICATIONS

Aquacultural Engineering May 2006; 34(3) : 224-233.*
(Continued)

*Primary Examiner* — Rob Swiatek
*Assistant Examiner* — Ebony Evans
(74) *Attorney, Agent, or Firm* — Holtz Holtz Goodman & Chick PC

(57) ABSTRACT

A method of manufacturing a column reactor for producing nitrate nitrogen as an inorganic nutrient from an organic material including: filling a container with a carrier comprising rockwool, vermiculite, pearlite, zeolite, sand, glass, ceramic, urethane, nylon, melamine resin, cedar chips, bog moss, filter paper or agar; adding thereto microorganisms capable of conducting a multiple parallel mineralization by mineralization of an organic material to produce nitrate nitrogen; subsequently adding 0.01 to 20 g in terms of dry weight of an organic material with respect to 1 L of the carrier, the organic material comprising fish-based soluble fertilizer, fish flour, oil cake, raw garbage, corn steep liquor, rice bran, soybean flour, plant residue, milk, powdered milk or livestock manure; and leaving the resultant material at rest until nitrate nitrogen starts to be produced in an effluent during a washing of the carrier by addition of water to discharge the effluent from the carrier.

6 Claims, 11 Drawing Sheets

(56) References Cited

U.S. PATENT DOCUMENTS

| | | | | |
|---|---|---|---|---|
| 4,284,508 | A | * | 8/1981 | Jewell .......................... 210/603 |
| 5,232,585 | A | * | 8/1993 | Kanow .......................... 210/151 |
| 5,656,059 | A | * | 8/1997 | Monster et al. ..................... 71/7 |
| 6,863,826 | B2 | * | 3/2005 | Sheets .......................... 210/705 |
| 7,350,331 | B1 | * | 4/2008 | Gontier et al. .................... 47/59 |
| 8,327,581 | B2 | * | 12/2012 | Shinohara et al. ............ 47/62 N |
| 2005/0054030 | A1 | * | 3/2005 | Schnoor et al. ................. 435/41 |
| 2005/0141966 | A1 | * | 6/2005 | Greene ................... 405/129.65 |
| 2011/0120005 | A1 | * | 5/2011 | King et al. ................... 47/62 N |

FOREIGN PATENT DOCUMENTS

| | | |
|---|---|---|
| JP | 2005-278523 A | 10/2005 |
| JP | 2007-119260 A | 5/2007 |

OTHER PUBLICATIONS

Makoto Shinohara, "Yuki Hiryo no Yoeki Saibai-Heiko Fukushiki Mukikaho ni yoru Yoekinai Biseibutsu Seitaikei Kochikuho-", ("Hydrphonics Using Organic Fertilizer"), *Agriculture and Horticulture*, 2006, 81 (7), p. 753-764.

Makoto Shinohara, "Yuki Hiryo de Yoeki Saibai . . . Kashika suru 'Ne' Konken Biseibutsu to Ne tono Sogo Sayo o Chokusetsu Kansatsu suru", *Kagaku to Seibutsu*, Apr. 2008, 46 (4), p. 230-232.

Makoto Shinohara, "Yoeki Saibai ni Okeru Yukibutsu o Katsuyo shita Konbu Byogai Yokushi Gijutsu", *Plant Protection*, 2007, 61(1), p. 17 to 20, I (1).

U.S. Appl. No. 13/056,120.

"Management of nutrients and solid media in drip Hydroponics" *Hakuyusha*, p. 119-155 (2005).

"Export of inorganic fertilizer produced from kitchen garbage and excrements", *Research Journal of Food and Agriculture*, vol. 31, p. 44-46 (2008).

* cited by examiner

METHOD FOR PRODUCING CARRIER ON WHICH MICROORGANISMS CAPABLE OF CONDUCTING MULTIPLE PARALLEL MINERALIZATION ARE IMMOBILIZED, COLUMN REACTOR AND SOLID MEDIUM FOR CULTIVATING PLANTS

This application is the United States national phase application of International Application PCT/JP2009/062868 filed Jul. 16, 2009.

TECHNICAL FIELD

The present invention relates to a method of manufacturing a carrier, on which microorganisms that can conduct a multiple parallel mineralization by mineralization of an organic material to produce nitrate nitrogen are immobilized.

The present invention also relates to a method of manufacturing a column reactor for producing nitrate nitrogen as inorganic nutrients from an organic material using the carrier. The present invention also relates to a method of manufacturing a solid medium for cultivating a plant, in which the carrier is used as the solid medium for cultivating a plant.

BACKGROUND ART

In recent years, movements of reducing the use of a chemical fertilizer and promoting the use of an organic fertilizer have been active worldwide from the viewpoint that a recycling society should be established.

However, in 'hydroponics' without the use of soil, which is increasingly used in the production of, for example, vegetables such as a tomato and flower and ornamental plants, the direct addition of an organic material to a nutrient solution generates a harmful intermediary metabolite, which damages the root of a plant. Hence, the utilization of the organic fertilizer in hydroponics has heretofore been unthinkable. Only the chemical fertilizer is therefore used in hydroponics at present.

There is a need for a technology for mineralizing an organic material to a useful inorganic nutrients such as nitrate nitrogen in order that the organic fertilizer is utilized in hydroponics. A conventional technology for mineralizing an organic material is, for example, a waste water treatment technology utilizing microorganisms (see, for example, Patent Literature 1). However, nitrate nitrogen is lost because such technology is accompanied by a denitrification involving reducing produced nitrate nitrogen to release nitrogen gas. Accordingly, the technology does not meet the purpose of manufacturing an inorganic fertilizer.

In view of the foregoing, the multiple parallel mineralization method described in each of Patent Literature 2 and Non Patent Literature 1 has been invented as a technology capable of efficiently collecting nitrate nitrogen (as a nitrate ion) from an organic material to be utilized as inorganic nutrients.

The technology is a highly reproducible method capable of degrading organic nitrogen while suppressing the denitrification, and collecting a nitrate ion which is nitrate nitrogen as inorganic nutrients with high efficiency, and is an unprecedented technology. This has allowed "hydroponics employing an organic fertilizer" and "manufacture of an inorganic fertilizer containing nitrate nitrogen using an organic material as a raw material", both of which have been hitherto difficult to be achieved (see, for example, Non Patent Literatures 1 and 3).

The invention described in Patent Literature 2 has gained a great deal of attention as a technology for realizing hydroponics employing an organic fertilizer, and manufacturing inorganic nutrients such as nitrate nitrogen using an organic resource as a raw material. Therefore, the invention has had high expectations from, for example, a company which plans to recycle an organic resource in addition to a farm or a plant factory having an interest in the invention as a novel hydroponics technology.

Further, the utilization of the multiple parallel mineralization method described in Patent Literature 2 allowed 'water culture using an organic fertilizer' to be performed by directly adding an organic fertilizer to a nutrient solution to produce nitrate nitrogen.

However, when a fertilizer containing inorganic nutrients is manufactured by the multiple parallel mineralization method described in Patent Literature 2, during the degradation of an organic material (ammonification) and the production of nitrate ion (nitrification), nitrification is conducted by only the action of microorganisms attached on a culture tank wall surface in a culture tank, and hence, the surface area of the wall surface determines the rate of a reaction. Accordingly, there has been a problem in that a very long time is required in terms of the rate of a reaction of mineralizing an organic material to nitrate nitrogen.

In addition, the culture and reaction of the microorganisms require constant aeration (operation of constantly keeping an aerobic condition through aeration or the like). Thus, an electrical power cost may be a problem when a large-scale treatment is assumed. Therefore, in the production of nitrate nitrogen as inorganic nutrients from an organic material, there has been a demand for the development of a method capable of remarkably enhancing the rate of a reaction (efficiently) and being performed without requiring aeration and constant electrical power.

By the way, in the case of performing hydroponics using a solid medium such as rockwool which is often utilized in, for example, the cultivation of a tomato ('hydroponics with solid medium cultivation'), there has been a problem in that, when an organic fertilizer is directly added to a nutrient solution, nitrate nitrogen is hardly produced because of the putrefaction of an organic material due to its insufficient degradation (see, for example, Non Patent Literature 2).

In view of the foregoing, studies have been made on the utilization of the multiple parallel mineralization method described in Patent Literature 2. However, also in this case, when an organic fertilizer is directly added to a nutrient solution, an organic component is present in the nutrient solution in a dissolved state, which may cause the clogging in a drip tube or a solid medium, and may cause problems such as the putrefaction of an organic material that has caused the clogging in the solid medium. Hence, there has been a problem in that the method itself is difficult to be put into practical use.

Accordingly, in order that the method described in Patent Literature 2 is utilized to perform solid medium cultivation, it is necessary to completely mineralize an organic material into an inorganic nutrient solution (nutrient solution containing an organic component at as low a concentration as possible) prior to being used for the nutrient solution in solid medium cultivation.

Therefore, in this case, a preparative operation to be performed before cultivation is complicated and requires a long time. Thus, there has been a demand for the development of a technology that allows an organic fertilizer to be employed in solid medium cultivation by a more simple method.

It should be noted that, although methods involving fixing microorganisms on a solid medium have been conventionally known (see, for example, Patent Literature 1), those methods are each accompanied by a denitrification to lose a fertilizer component (nitrate nitrogen), and hence such solid medium has not been able to be utilized to perform hydroponics by directly adding an organic fertilizer.

[Patent Literature 1] JP 2001-300583 A
[Patent Literature 2] JP 2007-119260 A
[Non Patent Literature 1] "Hydroponics using organic fertilizer", Agriculture and horticulture, Vol. 81, p. 753-764 (2006)
[Non Patent Literature 2] "Management of nutrients and solid media in drip Hydroponics" Hakuyusha, p. 119-155 (2005)
[Non Patent Literature 3] "Export of inorganic fertilizer produced from kitchen garbage and excrements" Research journal of food and agriculture, Vol. 31, p. 44-46 (2008)

DISCLOSURE OF THE INVENTION

Problem to be solved by the Invention

An object of the present invention is to provide a method of efficiently producing nitrate nitrogen as inorganic nutrients from an organic material without performing any operation using constant electrical power such as aeration in order to solve the above-mentioned conventional problems.

Another object of the present invention is to provide a method of manufacturing a solid medium for cultivating a plant, which allows hydroponics to be performed through the direct addition of an organic fertilizer even in the case of performing hydroponics with solid medium cultivation.

Means for solving the Problems

The inventor of the present invention has found that the reaction rate of a multiple parallel mineralization can be remarkably improved without performing any operation using constant electrical power such as aeration by immobilizing, on a carrier having ventilation, microorganisms that can conduct a multiple parallel mineralization by mineralizing an organic material to produce nitrate nitrogen, and using the carrier as a column reactor for conducting a multiple parallel mineralization, and nitrate nitrogen as inorganic nutrients can be efficiently produced from an organic material.

The inventor of the present invention has also found that the use of the carrier as a solid medium for cultivating a plant allows hydroponics to be performed by directly adding an organic fertilizer even in the case of performing hydroponics with solid medium cultivation.

The present invention has been completed based on those findings.

That is, a first aspect of the present invention is a method of manufacturing a carrier on which microorganisms capable of conducting a multiple parallel mineralization are immobilized, the method comprising: filling a container with a carrier having ventilation; adding thereto microorganisms that can conduct a multiple parallel mineralization by mineralization of an organic material to produce nitrate nitrogen; and subsequently adding an organic material and then leaving at rest until nitrate nitrogen starts to be produced in an effluent during washing the carrier through the addition of water to discharge the effluent from the carrier; thereby immobilizing the microorganisms capable of conducting a multiple parallel mineralization.

A second aspect of the present invention is the method of manufacturing a carrier according to the first aspect, in which the container is equipped with a drain outlet, and the effluent is discharged from the drain outlet.

A third aspect of the present invention is a method of manufacturing a carrier on which microorganisms capable of conducting a multiple parallel mineralization are immobilized, the method comprising: integrally molding a solid support having gas permeability so as to maintain a solid shape; adding thereto microorganisms that can conduct a multiple parallel mineralization by mineralization of an organic material to produce nitrate nitrogen; and subsequently adding an organic material and then leaving at rest until nitrate nitrogen starts to be produced in an effluent during washing the carrier through the addition of water to discharge the effluent from the carrier; thereby immobilizing the microorganisms capable of conducting a multiple parallel mineralization.

A fourth aspect of the present invention is the method of manufacturing a carrier according to any one of the first to third aspects, the method comprising repeatedly performing treatments of adding the organic material, then leaving at rest, and washing the carrier through the addition of water to discharge an effluent from the carrier, before nitrate nitrogen starts to be produced in the effluent discharged during washing the carrier.

A fifth aspect of the present invention is the method of manufacturing a carrier according to any one of the first to fourth aspects, in which the leaving at rest is performed until a nitrate ion starts to be produced at a concentration of 50 mg/L or more in the effluent.

A sixth aspect of the present invention is the method of manufacturing a carrier according to any one of the first to fifth aspects, in which the carrier is one or more kinds of porous carriers selected from the group consisting of rockwool, vermiculite, pearlite, zeolite, sand, Kanuma soil, glass, ceramic, urethane, nylon, a melamine resin, wood chips, straw, bog moss, charcoal, cotton, paper, a polyacrylamide gel, and agar.

A seventh aspect of the present invention is the method of manufacturing a carrier according to any one of the first to sixth aspects, comprising, when nitrate nitrogen is contained in the carrier in an amount of 10 mg or more in terms of a nitrate ion with respect to 1 L of the carrier immediately after adding the microorganisms, washing the carrier through the addition of water to discharge an effluent from the carrier, thereby removing nitrate nitrogen, in which an ammonification reaction and a nitrification reaction proceed without causing the accumulation of intermediate products and a denitrification does not proceed in the carrier during adding the organic material.

An eighth aspect of the present invention is the method of manufacturing a carrier according to any one of the first to seventh aspects, in which the microorganisms capable of conducting a multiple parallel mineralization is derived from one or more kinds of microorganism sources including microorganisms capable of conducting ammonification and microorganisms capable of conducting nitrification, the microorganism sources being selected from the group consisting of a culture solution obtained by culturing microorganisms capable of conducting a multiple parallel mineralization, dried microbial cells of the microorganisms obtained by drying the culture solution, the carrier on which microorganisms are immobilized, an effluent discharged from the carrier by adding water to the carrier on which microorganisms are immobilized, soil, tap water, water from lake and marsh, spring water, well water, river water, and sea water.

A ninth aspect of the present invention is the method of manufacturing a carrier according to any one of the first to eighth aspects, in which an amount of the organic material is 0.1 to 10 g with respect to 1 L of the carrier.

A tenth aspect of the present invention is the method of manufacturing a carrier according to any one of the first to ninth aspects, in which the organic material is a nitrogen-rich organic material having a content ratio of carbon to nitrogen, a C/N ratio, of 19 or less.

An eleventh aspect of the present invention is a method of manufacturing a carrier, in which the nitrogen-rich organic material according to the tenth aspect is one or more kinds selected from the group consisting of fish-based soluble fertilizer, fish flour, oil cake, raw garbage, corn steep liquor, rice bran, soybean flour, a plant residue, milk, powdered milk, and livestock manure.

A twelfth aspect of the present invention is a method of manufacturing a column reactor for producing nitrate nitrogen as inorganic nutrients from an organic material, in which the carrier obtained by the method according to anyone of the first to eleventh aspects is used as a column reactor for conducting a multiple parallel mineralization.

A thirteen aspect of the present invention is a fertilizer, which contains nitrate nitrogen as inorganic nutrients and is produced by using the column reactor obtained by the method according to the twelfth aspect.

A fourteenth aspect of the present invention is a method of cultivating a plant, in which the fertilizer containing nitrate nitrogen according to the thirteenth aspect is used.

A fifteenth aspect of the present invention is a method of manufacturing a solid medium for cultivating a plant, in which the carrier obtained by the method according to any one of the first to eleventh aspects is used as the solid medium for cultivating a plant.

A sixteenth aspect of the present invention is a solid medium for cultivating a plant, which is obtained by the method according to the fifteenth aspect.

A seventeenth aspect of the present invention is a method of cultivating a plant, comprising using the solid medium for cultivating a plant according to the sixteenth aspect and performing hydroponics by directly adding an organic fertilizer.

An eighteenth aspect of the present invention is the method of cultivating a plant according to the fourteenth to seventeenth aspects, in which the plant is a leaf vegetable, a fruit vegetable from which a fruit is harvested, a flower and ornamental plant, a tree, or a fruit tree.

Effects of the Invention

The present invention allows providing the column reactor capable of remarkably improving the reaction rate of a multiple parallel mineralization, and capable of efficiently producing nitrate nitrogen as inorganic nutrients from an organic material.

Thus, the present invention allows efficiently producing a fertilizer containing nitrate nitrogen as inorganic nutrients from an organic material using an organic resource or an organic fertilizer as a raw material without performing any operation using constant electrical power such as aeration.

The present invention also allows performing hydroponics through the direct addition of an organic fertilizer even in the case of performing hydroponics with solid medium cultivation.

BEST MODE FOR CARRYING OUT THE INVENTION

The present invention relates to a method of manufacturing a carrier on which microorganisms that can conduct a multiple parallel mineralization by mineralization of an organic material to produce nitrate nitrogen are immobilized.

The present invention also relates to a method of manufacturing a column reactor for producing nitrate nitrogen as inorganic nutrients from an organic material using the carrier. The present invention also relates to a method of manufacturing a solid medium for cultivating a plant, in which the carrier is used as the solid medium for cultivating a plant.

It should be noted that FIG. 1 is a diagram illustrating one aspect of a method of immobilizing microorganisms on a carrier, and FIG. 2 is a diagram illustrating one aspect of a column reactor for producing nitrate nitrogen as inorganic nutrients from an organic material.

In the present invention, a carrier on which microorganisms capable of conducting a multiple parallel mineralization are immobilized is manufactured by: filling a container with a carrier having ventilation; adding thereto microorganisms that can conduct a multiple parallel mineralization by mineralization of an organic material to produce nitrate nitrogen; and subsequently adding an organic material and then leaving at rest until nitrate nitrogen starts to be produced in an effluent during washing the carrier through the addition of water to discharge the effluent from the carrier.

It should be noted that, in the present invention, when a carrier integrally molded so as to maintain a solid shape is used, the carrier on which microorganisms capable of conducting a multiple parallel mineralization are immobilized may also be manufactured without filling the container with the carrier.

That is, the manufacture may be performed by: preparing a carrier having ventilation integrally molded so as to maintain a solid shape; adding thereto microorganisms that can conduct a multiple parallel mineralization by mineralization of an organic material to produce nitrate nitrogen; and subsequently adding an organic material and then leaving at rest until nitrate nitrogen starts to be produced in an effluent during washing the carrier through the addition of water to discharge the effluent from the carrier.

A first step in the manufacture of the carrier on which microorganisms capable of conducting a multiple parallel mineralization are immobilized of the present invention is a step of first filling a container with a carrier having ventilation (filling step).

It should be noted that a step of microbial inoculation as the subsequent step may also be performed without performing the filling step of filling the container by stacking carriers (specifically, stacking carriers each having ventilation on a planar structure, such as forming a stack of carriers) so that the stack of the carriers does not fall down during performing an operation of directly adding water to the stack of the carriers to discharge an effluent.

Further, also when the carrier integrally molded so as to maintain a solid shape is used, the step of microbial inoculation as the subsequent step may be directly performed without performing the filling step of filling the container.

In the present invention, any carrier may be used as the carrier, on which microorganisms are immobilized, as long as the carrier is able to support microorganisms, an organic component, and water, has ventilation, and is porous. Particularly preferred is a carrier made of a raw material having a large ratio of a surface area for immobilization (fixation) of microorganisms with respect to a volume.

It should be noted that the phrase "having ventilation" as used herein means that the environment of voids between and/or in the carriers in the case of filling a column (columnar container) with carriers or in the case of stacking the carriers to form a stack of the carriers, or the environment of voids in the carrier in the case of using the carrier integrally molded so as to maintain a solid shape is such a state that a gas phase is ensured so that nitrification easily proceeds and a denitrification hardly occurs owing to the maintenance of an aerobic condition.

It should be noted that the entire environment between and in the carriers may hereinafter be simply referred to as "in the carrier" or "the entire carrier".

Specific examples of such carrier which may be used include: rock and mineral-based materials such as rockwool, vermiculite, pearlite, zeolite, sand, Kanuma soil, glass (specifically glass beads), and ceramic; synthetic resin-based materials such as urethane, nylon, a melamine resin, and a polyacrylamide gel; biological materials such as wood chips (specifically Japanese cedar chips), straw, bog moss, charcoal (specifically activated charcoal), cotton, paper (specifically filter paper), and agar.

In the present invention, of those raw materials, it is preferred to use rockwool, vermiculite, pearlite, urethane, Japanese cedar chips, straw, bog moss, or filter paper, and it is more preferred to use rockwool or urethane.

It should be noted that the use of general soil as the carrier is not preferred because the addition of an organic material and water easily causes the excessive propagation of microorganisms, which leads to a deterioration in ventilation, a denitrification is caused by denitrifying microorganisms living in the soil, and finally no nitrate nitrogen is produced.

It should be noted that the carrier integrally molded so as to maintain a solid shape may be any carrier which is formed into, for example, a cubic shape, a globular shape, a cylindrical shape, or a rod-like shape so that the entire carrier has a single structure, or is integrally molded by being subjected to welding, adhesion, or pressure bonding with moderate heat.

Specifically, there may be used a raw material which can be handled as an integral carrier as it is, or can be integrally molded by adhesion or the like, being made of the raw materials such as rockwool, vermiculite, pearlite, zeolite, sand, Kanuma soil, glass (specifically glass beads), urethane, nylon, a melamine resin, wood chips (specifically Japanese cedar chips), straw, bog moss, charcoal (specifically activated charcoal), cotton, paper (specifically filter paper), a polyacrylamide gel, and agar each molded as described above. It is preferred to use rockwool.

Further, the size of the carrier integrally molded so as to maintain a solid shape is specifically any size of 10 ml or more in terms of a volume, but is not limited thereto.

Any container may be used as a container to be filled with the carrier as long as the container can be filled with the carrier and can discharge water after the addition of water.

The container is preferably any container that is equipped with a drain outlet and has a structure capable of efficiently discharging water after the addition of water (has a structure capable of being used as a column after filling with the carrier). Specific examples of the container which may be used include a container having a structure like a cup, in which an opening exists in an upper part, a container having a structure like a column, in which an opening exists in a lower part, and a container having a net-like overall structure.

It should be noted that, even when the container is not a container equipped with a drain outlet, any container capable of performing an operation such as tilting the container to perform an operation of discharging water (decantation) may be used.

In filling the container with the carrier, voids (gas phases) between and/or in the carriers are ensured in order to prevent the whole system from being water-logged owing to a capillary phenomenon after the addition of water to discharge an effluent. The height h (unit m) of a solution surface elevated due to a capillary phenomenon is given based on the following formula (I). It should be noted that the respective symbols in the formula (I) are as follows: T represents surface tension (N/m); θ represents a contact angle; ρ represents a liquid density (kg/m³); g represents gravitational acceleration (m/s²); and r represents an inner diameter (radius) (m) of a tube.

[Math. 1]

$$h = 2T \cos \theta / \rho g r \qquad (I)$$

When the voids between and/or in the carriers become narrower and the rise height h exceeds the filling height of the carriers, even if a drain outlet is opened in the case of adding water, the whole carrier is water-logged and left under an anaerobic state, and the progression of nitrification may become insufficient.

Therefore, it is desirable that such a size that the rise height h does not exceed the filling height be ensured for the voids between and/or in the carriers, and it is not preferred that all the voids become narrower and the rise height h exceed the filling height of the carriers.

It is most preferred to ensure both ventilation and water holding capacity in the entire carrier by allowing to have various size of voids between and/or in the carriers, to thereby ensure ventilation in a low-density portion having large voids and to ensure water holding capacity in a high-density portion having narrow voids.

When the voids between and/or in the carriers are narrow and the rise height h exceeds the filling height of the carriers, it is necessary to make attempts such as forming the wall surface of the container with a raw material or structure (net-like) having ventilation to facilitate gas exchange, or alternatively such as increasing the concentration of dissolved oxygen in water to be added, or exchanging water to be added with high frequency to promote gas exchange.

It should be noted that, when the container is filled with the carrier in consideration of the foregoing as a specific embodiment, the container may be filled with the carrier in a volume of 0.1 to 100,000 ml, preferably 1 to 10,000 ml. The container may also be filled with the carrier so that a layer having the filling height of 0.1 to 100 cm is achieved.

After the container has been filled with the carrier in the above-mentioned filling step, a step of adding microorganisms that can conduct a multiple parallel mineralization by mineralization of an organic material to produce nitrate nitrogen (step of microbial inoculation) is performed.

It should be noted that, as described above, in the case of stacking the carriers instead of filling a container with the carriers or in the case of using the carrier integrally molded so as to maintain a solid shape as the carrier, the step of microbial inoculation may be directly performed without performing the above-mentioned filling step.

In the present invention, the "multiple parallel mineralization" refers to a reaction by which an organic material is mineralized to produce nitrate nitrogen, wherein the degradation of an organic material to ammonium nitrogen (ammonification) and the nitrification of ammonium nitrogen to nitrate nitrogen (nitrification) are continuously performed in the same reaction system.

Specifically, the reaction refers to a reaction in which, in the degradation of an organic material, organic nitrogen contained in the organic material is degraded to ammonium nitrogen, and the ammonium nitrogen undergoes an oxidation reaction (nitrification reaction) through nitrification to produce nitrate nitrogen.

It should be noted that, in the present invention, nitrate nitrogen to be produced by mineralizing an organic material refers to a nitrate ion or a nitrate salt, and specifically assumed is a nitrate ion.

The microorganisms capable of conducting a multiple parallel mineralization in the present invention encompasses microorganisms capable of conducting ammonification and microorganisms capable of conducting nitrification.

The 'microorganisms capable of conducting a multiple parallel mineralization' which may be used in the present invention may be any microorganisms including microorganisms capable of conducting ammonification and microorganisms capable of conducting nitrification, and including microorganisms necessary for mineralizing an added organic material to produce nitrate nitrogen.

It should be noted that examples of the kind of the microorganisms forming the microorganisms described above include: microorganisms capable of conducting ammonification such as protozoans, bacteria, fungi, and any other ammonifying microorganisms; and microorganisms capable of conducting nitrification (nitrifying microorganisms) such as ammonium-oxidizing microorganisms (or nitrite-producing microorganisms) belonging to the genus *Nitrosomonas*, the genus *Nitorosococcus*, and the genus *Nitrosospira* (including the genus *Nitrosolobus* and the genus *Nitrosovibrio*) and nitrite-oxidizing microorganisms (or nitrate-producing microorganisms) belonging to the genus *Nitrobacter* and the genus *Nitrospira*.

There may be specifically used, as the microorganism source to be added in this step, a culture solution obtained by culturing microorganisms capable of conducting a multiple parallel mineralization, dried microbial cells of the microorganisms obtained by drying the culture solution, the carrier on which microorganisms are immobilized, an effluent discharged from the carrier by adding water to the carrier on which microorganisms are immobilized; and naturally-occurring microorganism sources such as soil, tap water, water from lake and marsh, spring water, well water, river water, and sea water.

In particular, it is preferred to use a culture solution obtained by culturing microorganisms capable of conducting a multiple parallel mineralization, dried microbial cells of the microorganisms obtained by drying the culture solution, the carrier on which microorganisms are immobilized, or an effluent discharged from the carrier by adding water to the carrier on which microorganisms are immobilized because the microorganisms forming a microorganism ecosystem required for the progression of a multiple parallel mineralization are contained in a sufficient amount, and a risk of inducing an denitrification is also small.

It should be noted that any carrier on which the microorganisms are immobilized may be used as 'the carrier on which microorganisms are immobilized', and it is preferred to use one manufactured through the steps of the present invention.

The denitrification refers to a phenomenon in which nitrate nitrogen is lost by the reduction of nitrate nitrogen to nitrous oxide gas, nitrogen gas, and the like by denitrifying microorganisms, and is a reaction that is easily induced in the coexistence of an organic component serving as an energy source for denitrifying microorganisms and nitrate nitrogen serving as an oxygen supplier for denitrifying microorganisms.

In the carrier of the present invention, the denitrification tends to occur in the case where an organic material is added before the addition of water to remove nitrate nitrogen in a carrier, to thereby establish the coexistence of an organic component and a high concentration of nitrate nitrogen, i.e., an condition under which the denitrification is easily induced, or in the case where small voids between and/or in the solid supports cause a capillary phenomenon to thereby bring into a water-logged state and an anaerobic condition in the solid support and satisfy the conditions inductive to the activities of denitrifying microorganisms.

In the present invention, the occurrence of the denitrification in the carrier is not preferred because nitrate nitrogen as excellent inorganic nutrients is lost by gasification. Therefore, in the present invention, for example, attention needs to be paid for the following: (i) when a high concentration of nitrate nitrogen is produced in a carrier, the carrier is washed through the addition of water to discharge an effluent from the carrier, to thereby remove nitrate nitrogen, (ii) an organic material is added after the removal of nitrate nitrogen has been performed by absorbing nitrate nitrogen as a fertilizer component by a plant and the like, and (iii) the entire carrier is prevented from being water-logged and left under an anaerobic state owing to a capillary phenomenon enhanced by an excessive decrease in size of the voids between and/or in the carriers.

The addition of the microorganism source to a container filled with the carrier is performed by adding a culture of microorganisms capable of conducting a multiple parallel mineralization when one wishes to immobilize the microorganisms in a short period of time. It should be noted that the microorganism source may also be added as the microorganism source in a liquid state or a powder state.

The addition amount of the microorganism source is not always particularly limited. The microorganism source is desirably added in an amount of 1 to 1000 ml in the case of a culture solution, 1 to 1000 mg in the case of dried microbial cells, and 1 to 1000 ml in the case of an effluent from the carrier with respect to 1 L of the carrier.

In this step, in the case where nitrate nitrogen is contained in the carrier owing to the use of a microorganism source containing nitrate nitrogen (or the use of a carrier containing nitrate nitrogen as the carrier filled in the previous step) as the microorganism source, it is preferred to wash the carrier through the addition of water to discharge an effluent from the carrier after the addition of the microorganism source.

It should be noted that the phrase "case where nitrate nitrogen is contained in the carrier" as used herein refers to a case where nitrate nitrogen is contained at such concentration and distribution that may induce a denitrification in the coexistence with an organic material.

That is, in this step, the case where nitrate nitrogen is 'not contained' in the carrier at such concentration and distribution that may induce a denitrification in the coexistence with an organic material is regarded as a "case where nitrate nitrogen is not contained in the carrier".

It should be noted that a specific operation of the "washing" is performed by (i) in the case of filling 'container equipped with a drain outlet' with the carrier, adding water and then discharging an effluent from the carrier through the drain outlet.

Further, the operation is performed by (ii) in the case of filling a 'container equipped with no drain outlet' with the carrier, adding water and then performing an operation such as tilting the container to discharge an effluent from the carrier (decantation).

Further, the operation is performed by (iii) in the case of stacking the carriers instead of filling a container with the carriers, or in the case of using, as the carrier, the 'carrier integrally molded so as to maintain a solid shape', adding water and then discharging an effluent from the carrier directly.

After the washing, the inside of the carrier is in a state in which a large amount of nitrate nitrogen has been removed, that is, a state in which nitrate nitrogen is not contained at such concentration and distribution that may induce a denitrification in the coexistence with an organic material. Further, the inside of the carrier is in a state in which excess water has been discharged.

Pure water (such as distilled water, ion-exchanged water, or reverse osmosis membrane-treated water), well water, river water, lake water, tap water, sea water, or the like may be used as water used in washing after the addition of the microorganism source. It should be noted that water containing nitrate nitrogen at a high concentration (specifically 50 mg $NO_3$/ml or more) is undesirable.

The water added to be used for the washing is desirably in an amount enough to rinse the entire carrier, and 100 to 10,000 ml per L is desirable.

The washing can remove nitrate nitrogen to decrease the concentration of nitrate nitrogen contained in a carrier. As a result, such a condition that may induce a denitrification (coexistence of an organic component and a high concentration of nitrate nitrogen) is not established, and a denitrification can be inhibited.

Accordingly, the inside of the carrier can be brought into a state in which an ammonification reaction and a nitrification reaction proceed without causing the accumulation of an intermediate product during the addition of an organic material and no denitrification occurs.

It should be noted that after the addition of the microorganism source, when 'nitrate nitrogen is not contained in the carrier at such concentration and distribution that may induce a denitrification in the coexistence with an organic material', the inside of the carrier is in a state in which no denitrification occurs even if the carrier is not washed, and hence washing does not need to be particularly performed.

After the addition of a microorganism source in the above-mentioned step of microbial inoculation, a step of: adding an organic material and then 'leaving at rest' until nitrate nitrogen starts to be produced in an effluent during washing the carrier through the addition of water to discharge the effluent from the carrier; thereby immobilizing the microorganisms capable of conducting a multiple parallel mineralization (immobilization step) is performed.

A carrier of interest on which microorganisms capable of conducting a multiple parallel mineralization are immobilized can be manufactured by the immobilization step.

This step is a step for immobilizing the microorganisms on the carrier through the fixation, acclimation, and growth.

In the immobilization step, the addition of an organic material is performed by directly adding an organic material to a carrier. It should be noted that the organic material may be added in a liquid state or in a powder state.

Any organic material such as an organic fertilizer and an organic resource such as a food residue, a plant residue, livestock waste, or excreta may be used as the organic material. It is desirable to use a nitrogen-rich organic material having a content ratio of carbon to nitrogen, a C/N ratio, of 24 or less, preferably 19 or less in order to increase in collection efficiency of nitrate nitrogen.

It is desired to use the organic material which abundantly contains a protein, a protein degradation product and an amino acid.

Specific examples thereof include food residues such as fish-based soluble fertilizer, corn steep liquor, oil cake, fish flour, soybean cake, yeast cake, sake cake, shochu cake, rice bran, and raw garbage. It should be noted that those are desirable because of being obtained as wastes in a food manufacturing process and being free of any component having toxicity. Further, a specific example thereof is livestock manure, and an organic material containing ammonium nitrogen may also be used. In addition, a food itself such as soybean flour, instant bouillon (containing an amino acid at a high concentration), milk, or powdered milk may also be utilized. In addition, a plant residue, which is a plant tissue or organ that cannot be utilized as an edible part, may also be utilized.

Of those, it is more desirable to use fish-based soluble fertilizer, fish flour, oil cake, raw garbage, corn steep liquor, rice bran, soybean flour, a plant residue, milk, powdered milk, or livestock manure.

It should be noted that a specific example of the fish-based soluble fertilizer is bonito-soluble fertilizer. Further, the corn steep liquid is, for example, corn steep liquor (CSL: corn steep liquid obtained as a by-product during manufacturing corn starch). Further, examples of the oil cake include rapeseed oil cake and corn oil cake. Further, examples of the plant residue include stems and leaves produced by a pruning treatment during the cultivation management of a tomato and the like. Further, examples of the raw garbage include bony fish parts, vegetable scraps and meat slices after cooking. Further, examples of the livestock manure include bovine manure and poultry manure.

It should be noted that bonito-soluble fertilizer or corn steep liquor is more particularly desirable because it is a liquid and easily permeates the carrier.

The organic material may be added in an amount of 0.01 to 20 g (in terms of dry weight), preferably 0.1 to 1 g (in terms of dry weight) with respect to 1 L of the carrier.

It should be noted that, specifically, when the organic material is in a liquid state, the amount is 0.1 to 20 g (liquid weight: (0.07 to 14 g in terms of dry weight)) in the case of using bonito-soluble fertilizer or is 0.1 to 20 g (liquid weight: (0.05 to 10 g in terms of dry weight)) in the case of using corn steep liquor.

It should be noted that the addition amount of the organic material exceeding the above-mentioned predetermined amount is not preferred because the amount may exceed the amount of the organic material which can be supported by the carrier. Further, the addition amount of the organic material below the above-mentioned predetermined amount is not preferred because the concentration of nitrate nitrogen is low to be collected as a fertilizer component.

Next, after the addition of an organic material, "leaving at rest" is conducted for the fixation, acclimation, and growth of the microorganisms.

The temperature during leaving at rest is a temperature of 10 to 42° C., preferably 15 to 37° C. suitable for the growth of microorganisms capable of conducting ammonification and microorganisms capable of conducting nitrification. It should be noted that a temperature lower than 10° C. is not preferred because a long time is required for immobilization owing to the growth retardation of microorganisms. Further, a temperature higher than 37° C. is not preferred because part of microorganisms necessary for conducting a multiple parallel mineralization may be killed.

With regard to the period of time required for "leaving at rest" in this step, the carrier is left at rest for a period of time 'until nitrate nitrogen starts to be produced in an effluent during washing the carrier through the addition of water to discharge the effluent from the carrier', i.e., a period of time 'until an assessment is made that the microorganisms have been immobilized on the carrier (through the fixation, acclimation, and growth).

The period of time required for "leaving at rest" in this step is specifically overnight (about 8 to 24 hours) or more, preferably 3 days or more, more preferably 5 days or more, most preferably 7 days or more in the case of using, as a microorganism source, a culture solution obtained by culturing microorganisms capable of conducting a multiple parallel mineralization, dried microbial cells of the microorganisms obtained by drying the culture solution, the carrier on which microorganisms are immobilized, an effluent discharged from the carrier by adding water to the carrier on which microorganisms are immobilized, or the like.

Further, it takes about 5 days or more, preferably 7 days or more, more preferably 2 weeks or more to complete the step in the case of using a naturally-occurring microorganism source as the microorganism source.

It should be noted that the case where a period of time required for leaving at rest in this step is shorter than a period of time taken until nitrate nitrogen starts to be produced is not preferred because ammonium nitrogen is mainly produced owing to the insufficient adaptation of microorganisms capable of conducting nitrification (nitrifying microorganisms).

Next, after having been left at rest as described above, the carrier is "washed" through the addition of water to discharge an effluent from the carrier.

It should be noted that a specific operation of the "washing" is performed by (i) in the case of filling 'container equipped with a drain outlet' with the carrier, adding water and then discharging an effluent from the carrier through the drain outlet.

Further, the operation is performed by (ii) in the case of filling a 'container equipped with no drain outlet' with the carrier, adding water and then performing an operation such as tilting the container to discharge an effluent from the carrier (decantation).

Further, the operation is performed by (iii) in the case of stacking the carriers instead of filling a container with the carriers, or in the case of using, as the carrier, the 'carrier integrally molded so as to maintain a solid shape', adding water and then discharging an effluent from the carrier directly.

After the washing, the inside of the carrier is in a state in which excess water has been discharged as well.

It should be noted that, after the washing, it is suitable to keep the environment in the carrier in an aerobic state (the carrier may be dried out) in order to inhibit the propagation of microorganisms capable of conducting a denitrification (denitrifying microorganisms).

Pure water (such as distilled water, ion-exchanged water, or reverse osmosis membrane-treated water), well water, river water, lake water, tap water, sea water, or the like may be used as water used in washing after leaving at rest. It should be noted that water containing nitrate nitrogen at a high concentration (50 mg $NO_3$/ml or more) is undesirable.

The addition amount of water used for the washing is desirably 100 to 3000 ml per L of the carrier.

The washing can remove nitrate nitrogen produced in the carrier to decrease the concentration of nitrate nitrogen contained in the carrier. As a result, such a condition that may induce a denitrification (condition in which an organic component and a high concentration of nitrate nitrogen coexist) is not established, and a denitrification can be inhibited.

Accordingly, the inside of the carrier can be brought into a state in which an ammonification reaction and a nitrification reaction proceed without causing the accumulation of an intermediate product during the addition of an organic material and no denitrification occurs.

Whether or not the microorganisms have been immobilized on the carrier (through the fixation, acclimation, and growth) may be assessed by measuring the concentration of nitrate nitrogen in an effluent during the washing.

That is, when a confirmation is made that 'nitrate nitrogen obtained by mineralizing an organic material has started to be produced in the effluent' by measuring the concentration of nitrate nitrogen in the effluent, it can be assessed that 'the microorganisms have been immobilized on the carrier'.

Further, preferably, when a nitrate ion is confirmed to be produced in the effluent at a concentration of 50 mg $NO_3$/L or more, more preferably 200 mg $NO_3$/L or more, it can be assessed that the microorganisms have been 'sufficiently' immobilized on the carrier.

As described above, in the carrier assessed to have immobilized thereon the microorganisms, the reaction rate (in particular, nitrification ability) of a multiple parallel mineralization in the carrier is remarkably improved. Therefore, an added organic material undergoes rapid degradation, leading to a state in which an organic component serving as an energy source for microorganisms capable of conducting a denitrification (denitrifying microorganisms) is lost at the time of the start of production of nitrate nitrogen. Thus, the inside of the carrier is under an environment in which a denitrification hardly occurs.

It should be noted that, when the microorganisms are not confirmed to have been immobilized (or 'sufficiently' immobilized) on the carrier, "treatments of adding the organic material and then leaving at rest and washing the carrier through the addition of water to discharge an effluent from the carrier" are repeatedly performed until the above-mentioned standard is satisfied.

That is, when nitrate nitrogen does not start to be produced in an effluent discharged during washing the carrier, the treatments are repeatedly performed until nitrate nitrogen starts to be produced in the effluent discharged during the washing.

As described above, the immobilization step is performed by (1) 'adding an organic material and then "leaving at rest" until nitrate nitrogen starts to be produced in an effluent during washing the carrier through the addition of water to discharge the effluent from the carrier' after a microorganism source has been added in the step of microbial inoculation. However, when immobilization of microorganisms is not confirmed on the carrier, the immobilization step is performed by (2) "repeatedly performing" treatments of 'adding the organic material and then leaving at rest and washing the carrier through the addition of water to discharge an effluent from the carrier' until nitrate nitrogen starts to be produced in the effluent discharged during the washing.

That is, the immobilization step may be performed using the operations (1) and (2) in combination.

Further, when a time required for leaving at rest in the operation (1) is prolonged like the predetermined period of time as described above, the step can be completed by washing only once after the addition of an organic material.

It should be noted that, in this step, in order to monitor the status of production of nitrate nitrogen contained in the effluent discharged during the washing, preferably, in order to confirm whether or not the microorganisms have been immobilized on the carrier, the "repetition" operation like the operation (2) may be performed.

It should be noted that, specifically, in the case of performing the "repetition" operation like the operation (2), the production of nitrate nitrogen may be grasped in detail by repeatedly performing the operation once 1 to 7 days, more preferably daily.

It should be noted that, from the viewpoint of suppressing the propagation of microorganisms capable of conducting a denitrification (denitrifying microorganisms), the frequency of the repetition operation like the operation (2) is preferably as low as possible. When the frequency of the "repetition" operation like the operation (2) is high, an anaerobic condition is easily established because the water content in a carrier is increased due to washing with high frequency. This suppresses activities of microorganisms capable of conducting nitrification (nitrifying microorganisms), with the result that the propagation of the microorganisms capable of conducting a denitrification (denitrifying microorganisms) is liable to occur.

A period of time required for completing the above-mentioned all steps, i.e., a period of time required for recognizing that the microorganisms have been immobilized or 'sufficiently' immobilized on the carrier is overnight (about 8 to 24 hours) or more, preferably 3 days or more, more preferably 5 days or more, most preferably 7 days or more in the case of using, as the microorganism source, a culture solution obtained by culturing microorganisms capable of conducting a multiple parallel mineralization, dried microbial cells of the microorganisms obtained by drying the culture solution, the carrier on which microorganisms are immobilized, an effluent discharged from the carrier by adding water to the carrier on which microorganisms are immobilized, or the like.

Further, in the case of using a naturally-occurring source as the microorganism source, it takes about 5 days or more, preferably 7 days or more, more preferably 2 weeks or more to complete the steps.

Thus, a carrier on which microorganisms capable of conducting a multiple parallel mineralization are immobilized can be manufactured.

Through the above-mentioned steps, the carrier on which the microorganisms capable of conducting a multiple parallel mineralization are immobilized (through the fixation, acclimation, and growth) can be used as a 'column reactor for producing nitrate nitrogen as inorganic nutrients from an organic material'.

It should be noted that, in the case of performing the above-mentioned steps using the container equipped with a drain outlet, the carrier may be used as a column reactor in a state in which the container equipped with a drain outlet is filled with the carrier.

Further, new another container filled with the carrier on which microorganisms are immobilized may also be used.

Further, also in the case of using the carrier integrally molded so as to maintain a solid shape without performing the filling step, the carrier on which microorganisms are immobilized may be used as a column reactor by appropriately cutting or grinding and being filled in new another container.

The column reactor of the present invention is any column reactor filled with 100 ml or more of the carrier on which microorganisms are immobilized when 1 g of the organic material is degraded.

Further, the column reactor of the present invention is filled so that the carrier functions as a column reactor, and both ventilation and water holding capacity are ensured by setting part of voids between or in the carriers to the sufficient size.

In other words, filling is performed so as to partially ensure such a void size (corresponding to r which is an inner diameter (radius) (m) of a tube) that the height h (unit m) of a solution surface elevated due to a capillary phenomenon (to be calculated with the above-mentioned formula (I)) does not exceed the filling height of a carrier. Further, during the filling, a carrier may be filled uniformly, but is more preferably filled ununiformly.

It should be noted that the case where all the voids between or in the carriers are small, and the height h (unit m) of a solution surface elevated due to a capillary phenomenon thus exceeds the filling height of a carrier is not preferred because addition of water to the column reactor may lead a waterlogged state and an anaerobic condition, and thus a denitrification is likely to be induced.

The use of the column reactor of the present invention can provide a fertilizer containing nitrate nitrogen as inorganic nutrients produced from an organic material.

A fertilizer containing a nitrate ion at a concentration of 50 mg $NO_3$/L or more, preferably 200 mg $NO_3$/L or more in an effluent from the column reactor is used as the fertilizer containing nitrate nitrogen as the inorganic nutrients.

Further, with regard to the amount of nitrate nitrogen as inorganic nutrients to be produced per day from an organic material in the case of using the column reactor of the present invention, nitrate nitrogen is produced in an amount of about 270 mg $NO_3$ or more in terms of a nitrate ion or about 60 mg N or more in terms of nitrogen with respect to 1 L of the carrier.

It should be noted that, even when a container is not filled with the carrier integrally molded so as to maintain a solid shape on which the microorganisms are immobilized, a fertilizer containing nitrate nitrogen as inorganic nutrients can be obtained by directly adding water to the carrier and collecting an effluent discharged from the carrier.

As for the amount of the organic material to be added during the manufacture of a fertilizer containing nitrate nitrogen as inorganic nutrients using the column reactor of the present invention, the organic material can be added in an amount of 0.01 to 20 g (in terms of dry weight), preferably 0.1 to 1 g (in terms of dry weight) with respect to 1 L of the carrier on which the microorganisms are immobilized. It should be noted that, specifically, when the organic material is in a liquid state, the amount is 0.1 to 20 g (liquid weight: (0.07 to 14 g in terms of dry weight)) in the case of using bonito-soluble fertilizer or 0.1 to 20 g (liquid weight: (0.05 to 10 g in terms of dry weight)) in the case of using corn steep liquor.

It should be noted that the addition amount of the organic material more than the above-mentioned predetermined amount is not preferred because a nitrification reaction cannot keep up with the amount, resulting in an increase in concentration of ammonium nitrogen in the effluent. In this regard, however, the addition amount is acceptable when a fertilizer having a high ammonium content ratio (e.g.: a fertilizer for soil cultivation) is intended to be manufactured.

The fertilizer containing nitrate nitrogen as inorganic nutrients may be used as a fertilizer for cultivating all plants such as a vegetable, a fruit, a flower and ornamental plant, a tree, and a foliage plant.

In particular, the fertilizer may be suitably used for cultivating: a leaf vegetable such as Chinese cabbage, komatsuna, lettuce, or spinach; a fruit vegetable from which a fruit is harvested such as a tomato; a flower and ornamental plant; and a fruit tree. In more particular, the fertilizer may be suitably used for cultivating a leaf vegetable such as Chinese cabbage or komatsuna.

It should be noted that the fertilizer containing nitrate nitrogen as inorganic nutrients may also be used in plant cultivation, which is generally performed, such as water culture, hydroponics with solid medium cultivation, or general soil cultivation.

As described above, the column reactor of the present invention can remarkably improve the reaction rate of a multiple parallel mineralization, and can efficiently produce nitrate nitrogen as inorganic nutrients from an organic material.

This is because a large surface area of catalyst and a high aerobic reaction condition can be ensured unlike a multiple parallel mineralization to be conducted in a water-logged state as a conventional method. That is, the use of a carrier on which the microorganisms have been immobilized at high density can increase a surface area for the catalyzation of a reaction, ensure water holding capacity through fine voids of the carrier (due to a capillary phenomenon: given water holding capacity is required for the growth of microorganisms), and simultaneously ensure ventilation through large voids (an aerobic reaction condition), to thereby activate microorganisms capable of catalyzing a multiple parallel mineralization and suppress a denitrification.

In addition, the use of the column reactor of the present invention can produce a fertilizer containing nitrate nitrogen as inorganic nutrients from an organic material without performing aeration or any other operation using constant electrical power (by an energy-saving method).

In particular, the use of the column reactor is advantageous during large-scale manufacture. This allows producing a fertilizer containing nitrate nitrogen as inorganic nutrients using a fertilizer containing an organic resource or an organic material as a raw material, and manufacturing and selling the product while keeping an operating cost and an installation cost at a low level in an organic waste treatment, which has not produced any valuable product heretofore despite requiring a high cost. This becomes a landmark technology in the waste treatment industry, which has not generated any benefit.

In addition, in the present invention, through the above-mentioned steps, the carrier on which the microorganisms capable of conducting a multiple parallel mineralization are immobilized (through the fixation, acclimation, and growth) may be used as a 'solid medium for cultivating a plant, which allows hydroponics by directly adding an organic fertilizer'.

That is, the use of the solid medium for cultivating a plant can perform 'hydroponics by directly adding an organic fertilizer even in solid medium cultivation'.

It should be noted that the hydroponics with solid medium cultivation may be performed by repeating an operation of directly adding an organic fertilizer to a solid medium after watering.

The addition of an organic fertilizer is performed by direct addition to the solid medium for cultivating a plant. It should be noted that the fertilizer containing an organic material may be added in a liquid state or a powder state.

As for an organic fertilizer which may be used by being directly added in the case of performing hydroponics using the solid medium for cultivating a plant, the above-mentioned organic material may be used as the fertilizer. However, it is preferred to use a liquid organic fertilizer whose addition operation is easily automated, that is, fish-based soluble fertilizer, corn steep liquor, or a suspension or putrefied solution obtained by finely pulverizing a solid organic material.

Further, an organic fertilizer is directly added to the solid medium for cultivating a plant. It should be noted that the fertilizer containing an organic material may be added in a liquid state or a powder state.

The organic fertilizer may be added in an amount of 0.01 to 20 g (in terms of dry weight), preferably 0.1 to 1 g (in terms of dry weight) with respect to 1 L of the carrier on which microorganisms are immobilized. It should be noted that, specifically, when the organic fertilizer is in a liquid state, the amount is 0.1 to 20 g (liquid weight: (0.07 to 14 g in terms of dry weight)) in the case of using bonito-soluble fertilizer or 0.1 to 20 g (liquid weight: (0.05 to 10 g in terms of dry weight)) in the case of using corn steep liquor.

It should be noted that the addition amount of an organic fertilizer more than the above-mentioned predetermined amount is not preferred because a nitrification reaction cannot keep up with the amount, resulting in an increase in concentration of ammonium nitrogen in the effluent. In this regard, however, such an addition amount that does not cause growth disorder during cultivation is acceptable.

It should be noted that, in the case of using the carrier on which microorganisms are immobilized as the solid medium for cultivating a plant, all of the raw materials for the carrier described above may be used as the carrier. Of those, it is particularly suitable to use preferably rockwool, vermiculite, pearlite, Kanuma soil, or urethane, more preferably to use rockwool.

In hydroponics by directly adding a fertilizer containing an organic material with a use of the solid medium for cultivating a plant, the carrier may be used for the cultivation of all plants such as a vegetable, a fruit, a flower and ornamental plant, a tree, a fruit tree, and a foliage plant.

In particular, the carrier may be suitably used for cultivating a plant including: a leaf vegetable such as Chinese cabbage, komatsuna, lettuce, or a herb; a fruit vegetable from which a fruit is harvested such as a tomato, an egg apple, a green pepper, a melon, a watermelon, or a strawberry; a flower and ornamental plant; and a fruit tree. In more particular, the carrier may be suitably used for cultivating a leaf vegetable such as Chinese cabbage or komatsuna.

In addition, in the present invention, the carrier on which microorganisms capable of conducting a multiple parallel mineralization are immobilized (through the fixation, acclimation, and growth) to be obtained through the above-mentioned step can be utilized as a microorganism material (microorganism source) capable of catalyzing a multiple parallel mineralization.

Specifically, the carrier may be utilized as a 'microorganism source' of microorganisms of a multiple parallel mineralization to be added in the filling step in the present invention. In addition, the carrier may be utilized as an 'inoculum of microorganisms optimized for a multiple parallel mineralization' in water.

EXAMPLES

Hereinafter, the present invention is described in more detail by way of examples. However, the present invention is by no means limited by these examples.

Example 1

Study 1 on Raw Material for Carrier

A study was made to determine whether or not an organic material was able to be mineralized to produce nitrate nitrogen by immobilizing microorganisms capable of conducting a parallel mineralization reaction on each of the raw materials for various carriers (granulated rockwool (manufactured by Grodan B.V.), vermiculite (manufactured by BS-lite Co., Ltd.), pearlite (manufactured by KOMERI Co., Ltd.), Kanuma soil (manufactured by Setogahara Kaen), and urethane (manufactured by WAKO Ltd.)).

First, 10 L of water were charged into a Wagner pot (manufactured by Fujiwara Scientific Co., Ltd.), 80 g of a bark compost (manufactured by Shimizu Port Lumber Industry Co-operative Association) and 8 g of bonito-soluble fertilizer (by-product from dried bonito factory, manufactured by Makurazaki Fisheries Cooperative Associations) (hereinafter, the same product is used unless otherwise indicated) were added thereto, and aeration with an air pump was performed to culture microorganisms capable of conducting a multiple parallel mineralization.

Next, the bottom of a 500-ml PET bottle was cut down to obtain the upper half portion of the bottle. The upper half portion was turned upside down leaving the lid of the pet bottle open, to thereby prepare a container in which the lid of the pet bottle served as a drain outlet. The container was filled with 100 ml of each of the various carriers described above.

Next, after 200 ml of the culture solution obtained by culturing the microorganisms capable of conducting a multiple parallel mineralization had been added and inoculated as a microorganism source, 100 ml of distilled pure water were added to discharge an effluent from the drain outlet, to thereby wash each of the various carriers described above.

After that, treatments of adding 0.1 g (liquid weight) of bonito-soluble fertilizer as an organic material, leaving at rest at room temperature (about 25° C.) overnight, and then washing with 100 ml of distilled pure water were repeated until the days described in FIG. 5 elapsed. It should be noted that, during washing, an effluent after the washing was collected to measure its nitrate ion concentration.

The measurement of nitrate ion concentration was performed by measurement with an RQ-flex (manufactured by Merck) using riflectoquant nitrate test strip (manufactured by Merck). (Hereinafter, in this example, a nitrate ion concentration was measured by the same method.)

Further, the container filled with each of the various carriers described above without the addition of the microorganism source was used as a control experiment (control). FIGS. 3(a) to 3(e) illustrate the results.

As a result, the production of a nitrate ion in the effluent was confirmed in any of the raw materials for the various carriers described above. In other words, the results showed that the microorganisms were immobilized on all of the raw materials for the various carriers described above to catalyze a multiple parallel mineralization. It should be noted that the production of a nitrate ion was not confirmed in the control experiment (control) without the addition of the microorganism source.

It should be noted that all of those raw materials for the various carriers described above were porous raw materials each having ventilation.

Further, the results of FIGS. 3(a) to 3(e) specifically showed that a nitrate ion was produced at a concentration of 30 mg/L or more in an effluent on Day 2 to Day 12 or later after the addition of the microorganism source.

In addition, the results showed that a nitrate ion was produced at a concentration of about 50 mg/L or more, in particular, about 70 mg/L or more in an effluent on Day 6 to Day 7 or later after the addition of the microorganism source in the case of using each of the various carriers described above excluding Kanuma soil, i.e., urethane, rockwool, pearlite, or vermiculite, and in more particular, a nitrate ion was produced at a concentration of about 200 mg/L or more in the case of using urethane or rockwool.

Those results are probably because those raw materials are raw materials each of which has particularly good ventilation and hardly undergoes a denitrification, and also because the surface area of those raw materials per volume is large enough to immobilize a number of microorganisms thereon, and hence a multiple parallel mineralization efficiently proceeds.

Accordingly, the results showed that a column reactor for producing nitrate nitrogen as inorganic nutrients from an added organic material was able to be manufactured in the case of using any raw materials for the various carriers described above.

Example 2

Inoculation of Dried Microbial Cells

An examination was made to determine whether or not dried microbial cells (not liquid) were able to be used as a microorganism source of microorganisms capable of conducting a multiple parallel mineralization.

A supernatant of the culture solution after the multiple parallel mineralization described in Example 1 was discarded, and a biofilm (microbial community structure) formed on a wall surface was dried by air drying to afford dried microbial cells of the microorganisms.

Next, the bottom of a 500-ml PET bottle was cut down to obtain the upper half portion of the bottle. The upper half portion was turned upside down leaving the lid of the pet bottle open, to thereby prepare a container in which the lid of the pet bottle served as a drain outlet. The container was filled with 20 g of granulated rockwool (volume of 100 ml).

After 10 mg of the dried microbial cells of the microorganisms had added and inoculated thereto as a microorganism source, 100 ml of distilled pure water were added to discharge an effluent from the drain outlet, to thereby wash the granulated rockwool.

After that, treatments of adding 0.1 g (liquid weight) of bonito-soluble fertilizer as an organic material, leaving at rest at 37° C. overnight, and then washing with 100 ml of distilled pure water were repeated for 2 days.

The resultant was then left at rest at 37° C. until the lapse of 22 days (until the lapse of 24 days after the addition of the microorganism source) without performing the treatments of adding bonito-soluble fertilizer and washing. After that, washing was performed with 100 ml of distilled pure water. It should be noted that, during washing, an effluent after the washing was collected to measure its nitrate ion concentration. FIG. 6 illustrates the results.

The results showed that, also when dried microbial cells were used and inoculated as the microorganism source, the microorganisms were immobilized on the granulated rockwool to catalyze a multiple parallel mineralization.

As evident from the results, the microorganism source having a shape of dried microbial cells may be inoculated.

Example 3

Study 2 on Raw Material for Carrier

In addition to the raw materials for the carriers described above, in order to make a further study to determine whether or not an organic material was able to be mineralized to produce nitrate nitrogen, the microorganisms capable of conducting a parallel mineralization reaction were immobilized on each of the fifteen different raw materials for carriers (5 g of straw (manufactured by Fujiwara Chemical Co., Ltd.), 2 g of bog moss (manufactured by KOMERI Co., Ltd.), 10 g of Japanese cedar chips (manufactured by Miura Shoji Co., Ltd.), 80 g of activated charcoal (manufactured by GEX. Co., Ltd.), 20 g of bamboo charcoal (manufactured by Sudo & Company, Inc.), 10 g of cotton (manufactured by Aisen Kougyou Co., Ltd.), 10 g of filter paper (manufactured by Advantec Toyo), 100 g of a 1.25% polyacrylamide gel (manufactured by Wako Pure Chemical Industries, Ltd.), 100 g of 1.6% agar (manufactured by Wako Pure Chemical Industries, Ltd.), 50 g of zeolite (manufactured by Takamura Ltd.), 50 g of sand (manufactured by Sudo & Company, Inc.), 50 g of ceramic (manufactured by Sudo & Company, Inc.), 60 g of glass beads (manufactured by Sudo & Company, Inc.), 6.3 g of nylon (manufactured by KOMERI Co., Ltd.), and 1 g of a melamine resin (manufactured by KOMERI Co., Ltd.)).

The bottom of a 500-ml PET bottle was cut down to obtain the upper half portion of the bottle. The upper half portion was turned upside down leaving the lid of the pet bottle open, to thereby prepare a container in which the lid of the pet bottle served as a drain outlet. The container was filled with each of the various carriers described above in the above-mentioned weight (amount corresponding to 20 to 100 ml).

Next, after 10 mg of the dried microbial cells of the microorganisms capable of conducting a multiple parallel mineralization used in Example 2 had been added and inoculated as a microorganism source, 100 ml of distilled pure water were added to discharge an effluent from the drain outlet, to thereby wash each of the various carriers described above.

After that, treatments of adding 0.1 g (liquid weight) of bonito-soluble fertilizer as an organic material, leaving at rest at about 37° C. overnight, and then washing with 100 ml of distilled pure water were repeated until the days described in FIG. 7 or FIG. 8 elapsed. It should be noted that, during washing, an effluent after the washing was collected to measure its nitrate ion concentration.

As a result, the production of a nitrate ion in the effluent was confirmed in any of 15 different raw materials for the various carriers described above. In other words, the results showed that the microorganisms were immobilized on all of the raw materials for the various carriers described above to catalyze a multiple parallel mineralization.

The results also showed that, of those, in particular, a nitrate ion was produced at a concentration of about 40 mg/L or more in an effluent on Day 8 or later after the addition of the microorganism source in the case of using nylon, bog moss, filter paper, Japanese cedar chips, sand, ceramic, or zeolite, and in more particular, a nitrate ion was produced at a concentration of about 50 mg/L or more (in particular, about 60 mg/L or more) in the case of using nylon, bog moss, filter paper, or Japanese cedar chips.

The results revealed that a naturally-occurring organic resin, a chemical resin, mineral matter such as glass or sand, ceramic, and the like were also able to be utilized as the raw materials for the carriers.

Example 4

Study 1 on Kind of Various Organic Materials

A study was made to determine whether or not an organic material was able to be mineralized to produce nitrate nitrogen by a multiple parallel mineralization in the case of using, as the organic material, any other organic material excluding bonito-soluble fertilizer used in Example 1 as well.

The bottom of a 500-ml PET bottle was cut down to obtain the upper half portion of the bottle. The upper half portion was turned upside down leaving the lid of the pet bottle open, to thereby prepare a container in which the lid of the pet bottle served as a drain outlet. The container was filled with 70 g of vermiculite (volume of 250 ml).

After 500 ml of the culture solution obtained by culturing the microorganisms capable of conducting a multiple parallel mineralization used in Example 1 had been added and inoculated thereto as a microorganism source, 250 ml of distilled pure water were added to discharge an effluent from the drain outlet, to thereby wash the vermiculite.

After that, treatments of adding, as an organic material, 0.2 g of rapeseed oil cake or 0.2 g (liquid weight) of corn steep liquor (CSL: corn steep liquid as a by-product during manufacturing corn starch), leaving at rest at room temperature (about 25° C.) overnight, and then washing with 250 ml of distilled pure water were repeated until the days described in each of FIG. 7 and FIG. 8 elapsed. It should be noted that, during washing, an effluent after the washing was collected to measure its nitrate ion concentration.

Further, the container filled with the vermiculite described above without the addition of the microorganism source was used as a control experiment (control). FIG. 9 illustrates the results in the case of adding rapeseed oil cake and FIG. 10 illustrates the results in the case of adding CSL.

As a result, the production of a nitrate ion in the effluent was confirmed in the case of using any of rapeseed oil cake and CSL as the organic material. In other words, the results showed that the microorganisms were immobilized on the vermiculite to catalyze a multiple parallel mineralization. It should be noted that the production of a nitrate ion was not confirmed in the control experiment (control) without the addition of the microorganism source.

In particular, the results showed that, when a liquid containing CSL was added continuously, a nitrate ion was produced at a stable concentration on each successive day on Day 6 or later after the addition of the microorganism source. The results revealed that the conversion efficiency of organic nitrogen contained in the CSL into nitrate nitrogen was 98.6% which was found to be extremely high.

Accordingly, the results showed that the addition of CSL as the organic material allowed the collection of an effluent containing nitrate nitrogen at a particularly high concentration.

Example 5

Study 2 on Kind of Organic Material

A further study was made to determine whether or not an organic material was able to be mineralized to produce nitrate nitrogen by a multiple parallel mineralization in the case of using any organic material excluding those described above as well.

The bottom of a 500-ml PET bottle was cut down to obtain the upper half portion of the bottle. The upper half portion was turned upside down leaving the lid of the pet bottle open, to thereby prepare a container in which the lid of the pet bottle served as a drain outlet. The container was filled with 10 g of granulated rockwool (volume of 50 ml).

After 10 mg of the dried microbial cells of the microorganisms capable of conducting a multiple parallel mineralization used in Example 2 had been added and inoculated thereto as a microorganism source, 100 ml of distilled pure water were added to discharge an effluent from the drain outlet, to thereby wash the granulated rockwool.

After that, treatments of adding, as an organic material, 0.1 g of fish flour (manufactured by Tosho), corn oil cake (manufactured by Tosho), or a food residue (raw garbage, nitrogen content of 6%) leaving at rest at 37° C. overnight, and then washing with 100 ml of distilled pure water were repeated until the days described in FIG. 9 elapsed. It should be noted that, during washing, an effluent after the washing was collected to measure its nitrate ion concentration. FIG. 9 illustrates the results.

As a result, the production of a nitrate ion in the effluent was confirmed in the case of using, as the organic material, any of fish flour (manufactured by Tosho), corn oil cake (manufactured by Tosho), and a food residue, suggesting that an effluent containing nitrate nitrogen was able to be collected.

Example 6

Study 3 on Kind of Organic Material)

A further study was made to determine whether or not an organic material was able to be mineralized to produce nitrate nitrogen by a multiple parallel mineralization in the case of using an organic material excluding those described above as well.

The bottom of a 500-ml PET bottle was cut down to obtain the upper half portion of the bottle. The upper half portion was turned upside down leaving the lid of the pet bottle open, to thereby prepare a container in which the lid of the pet bottle served as a drain outlet. The container was filled with 10 g of granulated rockwool (volume of 50 ml).

After 10 mg of the dried microbial cells the microorganisms capable of conducting a multiple parallel mineralization used in Example 2 had been added and inoculated thereto as a microorganism source, 100 ml of distilled pure water were added to discharge an effluent from the drain outlet, to thereby wash the granulated rockwool.

After that, treatments of adding, as an organic material, 0.1 g (liquid weight in the case of milk) of rice bran (manufactured by TSUKEMOTO Co., Ltd.), powdered milk (manufactured by Morinaga Milk Industry Co., Ltd.), instant bouillon (manufactured by Shimaya Co., Ltd.), soybean flour (manufactured by Safetek International, Inc.), milk (manufactured by Ouchiyamarakunou), plant stems and leaves (axillary buds of a tomato plant), bovine manure (manufactured by Tosho Co., Ltd.), or poultry manure (manufactured by Tosho Co., Ltd.), leaving at rest at room temperature (about 25° C.) overnight, and then washing with 100 ml of distilled pure water were repeated until the days described in FIG. 10 elapsed. It should be noted that, during washing, an effluent after the washing was collected to measure its nitrate ion concentration.

As a result, the production of a nitrate ion in the effluent was confirmed in the case of using any of the above-mentioned organic materials, suggesting that an effluent containing nitrate nitrogen was able to be collected.

It should be noted that the results revealed that, of those, rice bran, which had a C/N ratio (content ratio of nitrogen to carbon) as high as 18.1 and was an organic resource from which nitrate nitrogen was not able to be collected by a conventional multiple parallel mineralization in water, was able to be mineralized to produce nitrate nitrogen through the addition to the above-mentioned column.

The main reason is probably that the reaction rate of a multiple parallel mineralization in the carrier was remarkably improved as compared to that of a conventional multiple parallel mineralization in water. In other words, the reason is probably that an aerobic condition is constantly maintained because of high ventilation in the carrier, and that a surface area on which microorganisms capable of catalyzing a reaction have been immobilized is large, leading to a remarkable improvement in the rate of a degradation and nitrification reaction of an organic component. Further, another possible reason is that the diffusion of an organic component hardly occurs in the carrier, whereas ammonium easily diffuses by water supported by the carrier, which generates a localized site having a low C/N ratio.

Example 7

Utilization of Naturally-Occurring Microorganism Source

A study was made to determine whether or not a naturally-occurring microorganisms contained in soil, sea water, tap water, or the like was able to be utilized as a microorganism inoculum source to be immobilized on a carrier.

The bottom of a 500-ml PET bottle was cut down to obtain the upper half portion of the bottle. The upper half portion was turned upside down leaving the lid of the pet bottle open, to thereby prepare a container in which the lid of the pet bottle served as a drain outlet. The container was filled with 10 g of granulated rockwool (volume of 50 ml).

After 100 ml of sea water, 100 ml of tap water, or 1 g of soil had been added and inoculated thereto as a microorganism source, 100 ml of distilled pure water were added to discharge an effluent from the drain outlet, to thereby wash the granulated rockwool.

After that, treatments of adding 100 mg of bonito-soluble fertilizer as an organic material, leaving at rest at room temperature (about 25° C.) overnight, and then washing with 100 ml of distilled pure water were repeated until the days described in FIG. 11 or FIG. 12 elapsed. It should be noted that, during washing, an effluent after the washing was collected to measure its nitrate ion concentration.

Further, the container filled with the granulated rockwool described above with the addition of distilled pure water in place of the microorganism source was used as a control experiment (control). FIG. 11 illustrates the results in the case of inoculating sea water or tap water as the microorganism source, and FIG. 12 illustrates the results in the case of inoculating soil as the microorganism source.

As a result, the production of a nitrate ion in the effluent was confirmed in the case of adding and inoculating any of sea water, tap water, and soil as the microorganism source. In other words, the results showed that the naturally-occurring microorganisms were immobilized on the granulated rockwool to catalyze a multiple parallel mineralization. It should be noted that the production of a nitrate ion was not confirmed in the control experiment (control) in which distilled pure water was added in place of the microorganism source.

The results revealed that the utilization of the naturally-occurring microorganisms contained in soil, sea water, or tap water as the inoculum source allowed microorganisms capable of conducting a multiple parallel mineralization to be immobilized on a carrier.

In this regard, however, the results showed that the immobilization of microorganisms contained in sea water or tap water tended to require a longer time as compared to the case of using the culture solution of the microorganisms prepared in Example 1. The results revealed that the use of soil as the inoculum source allowed relatively rapid immobilization.

Example 8

Utilization of Column Effluent as Microorganism Source

An experiment was performed in which an effluent from a carrier on which the microorganisms capable of catalyzing a parallel mineralization reaction had been preliminarily immobilized (effluent from a column reactor filled with the carrier on which microorganisms are immobilized) was utilized as a microorganism source and immobilized on another carrier.

The bottom of a 500-ml PET bottle was cut down to obtain the upper half portion of the bottle. The upper half portion was turned upside down leaving the lid of the pet bottle open, to thereby prepare a container in which the lid of the pet bottle served as a drain outlet. The container was filled with 20 g of granulated rockwool (volume of 100 ml).

After 100 ml of the effluent from the column reactor filled with the granulated rockwool described in Example 1 had been added and inoculated thereto as a microorganism source, 100 ml of distilled pure water were added to discharge an effluent from the drain outlet, to thereby wash the granulated rockwool.

After that, treatments of adding 0.1 g (liquid weight) of bonito-soluble fertilizer as an organic material, leaving at rest at room temperature (about 25° C.) overnight, and then washing with 100 ml of distilled pure water were repeated until the days described in FIG. 13 elapsed. It should be noted that, during washing, an effluent after the washing was collected to measure its nitrate ion concentration.

Further, the container filled with the granulated rockwool described above without the addition of the microorganism source was used as a control experiment (control). FIG. 13 illustrates the results.

The results revealed that, when the 'effluent from the column reactor' filled with the granulated rockwool on which the microorganisms were immobilized described in Example 1 above was added as the microorganism source, the concentration of a nitrate ion produced in an effluent from the drain outlet showed as high a value as about 220 mg/L after the lapse of 7 days, and the rapid immobilization of microorganisms capable of conducting a multiple parallel mineralization was attained in the same manner as the case where the culture solution described in Examples 1 and 2 was used as the microorganism source.

It should be noted that the production of a nitrate ion was not confirmed in the control experiment (control) in which the microorganism source was not added.

The experimental results revealed that the effluent from the column reactor using the carrier on which the microorganisms had been preliminarily immobilized was able to be utilized as a microorganism source for another carrier.

Example 9

Study 1 on Immobilization without Using any Container

A study was made to determine whether or not the microorganisms were directly immobilized on a carrier integrally molded so as to maintain a solid shape without using the above-mentioned column mode (method involving filling a container equipped with a drain outlet with a carrier).

First, komatsuna was cultivated by water culture using the culture solution after the multiple parallel mineralization described in Example 1. After the cultivation, a 'culture solution of the microorganisms free of nitrate nitrogen' was obtained.

Next, a rockwool cube (manufactured by Grodan B.V., 100×100×100 mm: volume 1 L) integrally molded so as to maintain a solid shape was washed by directly adding 500 ml of distilled pure water to the rockwool cube to discharge excess water from the rockwool cube.

500 ml of the culture solution free of nitrate nitrogen were added and inoculated thereto as a microorganism source. It should be noted that the rockwool cube was not washed with distilled pure water after the addition of the microorganism source.

After that, 0.5 g of bonito-soluble fertilizer was added as an organic material, followed by 'leaving at rest until the lapse of 6 days' at room temperature (about 25° C.) and then washing with 500 ml of distilled pure water. A solution discharged from the rockwool cube was collected to measure its nitrate ion concentration. FIG. 16 illustrates the results.

The results showed that, also in the case of using rockwool (carrier) integrally molded so as to maintain a solid shape without the use of the above-mentioned column mode (method involving filling a container equipped with a drain outlet with a carrier), a nitrate ion was produced at a concentration of about 50 mg/L on Day 6 after the addition of the microorganism source.

In other words, the results showed that, when a carrier itself had a porous structure in which microorganisms, an organic material, and water were supported, the carrier integrally molded so as to maintain a solid shape was able to be directly subjected to a step of immobilizing microorganisms without being filled into a container.

Further, the results showed that, in the case of using a microorganism source free of a nitrate ion, the microorganisms were immobilized on the carrier to catalyze a multiple parallel mineralization even if the carrier (rockwool cube) was not washed with water after inoculation. The fact revealed that a washing operation with water after the addition of the microorganism source was able to be omitted in the case of using the microorganism source free of a nitrate ion.

Further, the results showed that, in this case, there was no need to repeat an operation of adding an organic material, followed by leaving at rest and washing with water, and the acclimation and growth of microorganisms were achieved by merely adding an organic material and leaving at rest for several days, to thereby promote the immobilization on a carrier.

A possible reason for the results is that the concentration of nitrate nitrogen in the carrier is low at the time of adding an organic material, which hardly induces a denitrification.

Example 10

Study 2 on Immobilization without Using any Container

A further study was made on a carrier integrally molded so as to maintain a solid shape without using the above-mentioned column mode (method involving filling a container equipped with a drain outlet with a carrier).

First, a rockwool cube (manufactured by Grodan B.V., 100×100×100 mm: volume 1 L), cotton (manufactured by Aisen Kougyou Co., Ltd., 20 g: volume 100 mL), and a melamine resin (manufactured by KOMERI Co., Ltd., 2 g: volume 50 mL) each integrally molded so as to maintain a solid shape were prepared. It should be noted that the cotton and the melamine resin were hung with strings (FIG. 17 show photographic images).

10 mg of the dried microbial cells of the microorganisms capable of conducting a multiple parallel mineralization used in Example 2 were added and inoculated thereto as a microorganism source. It should be noted that, in this example, the carrier was not washed with distilled pure water after the addition of the microorganism source because the addition amount itself of the microorganism source added was extremely small (i.e., because the amount of nitrate nitrogen contained in the microorganism source was also extremely small).

After that, treatments of adding 0.1 g of bonito-soluble fertilizer as an organic material, leaving at rest at 37° C.

overnight, and then washing with 100 ml of distilled pure water were repeated until the days described in FIG. 18 elapsed. It should be noted that, during washing, an effluent after the washing was collected to measure its nitrate ion concentration. FIG. 18 illustrates the results.

The results showed that, also in the case of using a carrier other than rockwool, i.e., cotton or a melamine resin, integrally molded so as to maintain a solid shape, the production of a nitrate ion was confirmed on Day 6 after the addition of the microorganism source.

In other words, the results showed that the microorganisms were able to be immobilized without causing any problem on any carrier such as a resin integrally molded so as to maintain a solid shape even when not being filled into a container.

It should be noted that the results showed that, of those, in the case of using rockwool, a nitrate ion was produced at a concentration of about 240 mg/L in an effluent on Day 8 after the addition of the microorganism source, and showed that the rockwool was particularly suitable as a raw material for a carrier on which the microorganisms were to be immobilized. This is presumably because the rockwool is a raw material excellent in terms of ventilation and surface area for the immobilization of microorganisms.

Example 11

Immobilization of Microorganisms Through Decantation

A study was made to determine whether or not the microorganisms were able to be immobilized on a carrier in the case of washing through decantation instead of the above-mentioned column mode (method of filling a container equipped with a drain outlet with a carrier).

10 g (50 ml in volume) of granulated rockwool were loaded into a plastic cup (200-ml volume). 10 mg of the dried microbial cells of the microorganisms capable of conducting a multiple parallel mineralization used in Example 2 were added and inoculated thereto as a microorganism source. It should be noted that, in this example, the carrier was not washed with distilled pure water after the addition of the microorganism source because the addition amount itself of the microorganism source added was extremely small (i.e., because the amount of a nitrate nitrogen contained in the microorganism source was also extremely small).

After that, treatments of adding 0.1 g of bonito-soluble fertilizer as an organic material, leaving at rest at 37° C. overnight, then adding 100 ml of distilled pure water, leaving at rest for a few minutes, and tilting the plastic cup to discharge excess water (washing treatment through decantation) were repeated until the days described in FIG. 16 elapsed. It should be noted that, during washing, an effluent after the washing was collected to measure its nitrate ion concentration.

The results showed that, also in the case of washing through decantation without the use of the above-mentioned column mode (method involving filling a container equipped with a drain outlet with a carrier), a nitrate ion was produced at concentrations of about 40 mg/L on Day 6 after the addition of the microorganism source and about 75 mg/L on Day 8 after the addition.

The fact showed that the microorganisms were able to be immobilized on the carrier by washing through decantation even when the carrier was not filled into a column (container equipped with a drain outlet).

Example 12

Hydroponics with Solid Medium Cultivation by Directly Adding Organic Fertilizer

A study was made to determine whether or not hydroponics in which a fertilizer containing an organic material was directly added in solid medium cultivation was attained by using a carrier on which the microorganisms capable of conducting a parallel mineralization reaction were immobilized as a solid medium for cultivating a plant.

After 500 ml of the culture solution obtained by culturing the microorganisms capable of conducting a multiple parallel mineralization used in Example 1 had been added and inoculated as a microorganism source to a rockwool cube (manufactured by Grodan B.V., 100×100×100 mm: volume 1 L, a carrier integrally molded so as to maintain a solid shape), 500 ml of tap water were added to discharge water from the rockwool cube, to thereby wash the rockwool cube. It should be noted that 20 containers filled with the rockwool were defined as one section.

After that, with respect to one section formed of the above-mentioned containers, treatments of adding 0.5 g (liquid weight) of bonito-soluble fertilizer as a liquid containing an organic material to each rockwool cube, leaving at rest at room temperature (about 25° C.) overnight, and then washing with 500 ml of tap water were repeated until the lapse of 7 days after the inoculation of the microorganisms.

Next, after the production of a nitrate ion in an effluent had been confirmed on Day 8 after the inoculation of the microorganisms, Chinese cabbage seeds were seeded to the rockwool cube. It should be noted that, after the seeding, the treatments of adding bonito-soluble fertilizer and washing were discontinued. The cultivation was performed in a glass greenhouse (equipped with no heater) on Dec. 6, 2007 to Jan. 9, 2008.

An operation that repeats the treatments of adding bonito-soluble fertilizer and washing was restarted on Day 10 after the seeding (on Day 18 after the addition of the microorganism source), i.e., at the stage of cotyledon development, and cultivation was conducted by performing the treatments of adding bonito-soluble fertilizer and washing with tap water twice a week until the lapse of 34 days after the seeding (until the lapse of 42 days after the addition of the microorganism source). This one cultivation section was defined as an 'inoculation and bonito-soluble fertilizer' section as a section of the present invention.

Further, another section was prepared in which the microorganism source was not added to the above-mentioned container filled with the rockwool cube, and was defined as a 'non-inoculation and bonito-soluble fertilizer' section as a control experiment.

In addition, still another section was prepared in which the microorganism source was not added to the above-mentioned container filled with the rockwool cube and a chemical fertilizer was added thereto in place of the liquid containing an organic material, and was defined as a 'chemical fertilizer' section as a control experiment. FIG. 20 show the results.

The results showed that Chinese cabbage in the 'inoculation and bonito-soluble fertilizer' section as the section of the present invention showed satisfactory growth at the same level as that of the 'chemical fertilizer' section.

Further, in the 'non-inoculation and bonito-soluble fertilizer' section (i.e., section in which cultivation was conducted with a rockwool cube without the inoculation of a microorganism source and with the addition of bonito-soluble fertilizer), the growth of Chinese cabbage was drastically delayed.

This is presumably because no microorganism source was inoculated, and hence the degradation of bonito-soluble fertilizer did not proceed beyond the stage of ammonification, resulting in a disorder due to excess ammonium.

Example 13

Growth Experiment Using Column Reactor Effluent 100 mg of bonito-soluble fertilizer were mineralized every day using granulated rockwool as a microbial carrier, and 100 ml of the resultant effluent were used for the growth experiment of komatsuna.

To the column reactor filled with granulated rockwool on which microorganisms capable of conducting a multiple parallel mineralization were immobilized obtained in Example 2, treatments of adding 100 mg of bonito-soluble fertilizer, leaving at rest at room temperature (about 25° C.) overnight, and then adding 100 ml of distilled pure water to collect an effluent (treatments for producing nitrate nitrogen as inorganic nutrients from an organic material) were repeated every day.

An operation of feeding 10 komatsuna seedlings with 100 ml of the effluent obtained every day as a fertilizer was repeated daily. (It should be noted that, in this case, a solution remaining from the previous day was discarded.) The seedlings were left at rest under conditions of 25° C. day and night and natural light.

Further, an operation of feeding 100 ml of distilled pure water containing 100 mg of bonito-soluble fertilizer was repeated daily as a control experiment.

The results revealed that, also in the case of using, as a fertilizer, an effluent containing nitrate nitrogen produced from an organic material using a column reactor filled with a carrier (granulated rockwool) on which microorganisms capable of conducting a multiple parallel mineralization were immobilized, komatsuna grew without causing any problem. In the control experiment, komatsuna scarcely grew, and a growth disorder appeared, which was estimated to be a disorder due to excess ammonium.

Example 14

Utilization 1 of Carrier on which Microorganisms are Immobilized as Microorganism Source A study was made to determine whether or not a carrier itself on which the microorganisms capable of conducting a parallel mineralization reaction had been preliminarily immobilized was able to be utilized as a microorganism source.

The bottom of a 500-ml PET bottle was cut down to obtain the upper half portion of the bottle. The upper half portion was turned upside down leaving the lid of the pet bottle open, to thereby prepare a container in which the lid of the pet bottle served as a drain outlet. The container was filled with 9 g of granulated rockwool.

After 1 g of the granulated rockwool on which the microorganisms had been preliminarily immobilized (ready to catalyze a multiple parallel mineralization) obtained in Example 1 had been added and inoculated thereto as a microorganism source (the volume of granulated rockwool finally reached 50 ml), 100 ml of distilled pure water were added to discharge an effluent from the drain outlet, to thereby wash the granulated rockwool.

After that, treatments of adding 0.1 g of bonito-soluble fertilizer as an organic material, leaving at rest at 37° C. overnight, and then washing with 100 ml of distilled pure water were repeated until the days set forth in FIG. 17 elapsed. It should be noted that, during washing, an effluent after the washing was collected to measure its nitrate ion concentration.

The results showed that, when the granulated rockwool on which the microorganisms were immobilized obtained in Example 1 was added as the microorganism source, a nitrate ion was produced at concentrations of about 20 mg/L on Day 6 after the addition and about 35 mg/L on Day 8 after the addition.

Accordingly, the results showed that the microbial carrier on which the microorganisms were immobilized were able to be utilized as a microorganism source for another unused carrier.

Example 15

Utilization 2 of Carrier on which Microorganisms are Immobilized as Microorganism Source A study was made to determine whether or not a carrier on which the microorganisms capable of conducting a parallel mineralization reaction had been preliminarily immobilized was able to be utilized as a microorganism source for a multiple parallel mineralization in water.

100 mL of distilled pure water were charged into a 500-ml Erlenmeyer flask, and 1 g of the granulated rockwool on which the microorganisms had been preliminarily immobilized (ready to catalyze a multiple parallel mineralization) obtained by adding soil as the microorganism source in Example 7 was taken out and added and inoculated as the microorganism source.

0.1 g of bonito-soluble fertilizer as an organic material was added thereto, culture was conducted at a water temperature of 25° C. while the flask being shaken at 120 rpm so that an aerobic condition was maintained until the days described in FIG. 18 elapsed, and the concentration of a nitrate ion was measured successively. FIG. 18 illustrates the results.

The results showed that a multiple parallel mineralization in water was able to be conducted by using, as the microorganism source, the carrier on which the microorganisms capable of conducting a parallel mineralization reaction had been preliminarily immobilized.

Industrial Applicability

The present invention allows an application to a technology for manufacturing an inorganic fertilizer using organic waste as a raw material. The waste recycling industry is predicted to grow to an industry with a market size of 2.5 trillion yen in the future. The present invention is a first technology for recycling an organic resource into an inorganic fertilizer and thus has very large industrial applicability.

Further, a conventional technology requires much aeration, and thus requires power such as an air pump. In contrast, the present invention allows the column mode to be employed, and thus allows an energy-saving degradation method without requiring electrical power. This is also highly attractive.

The present invention also allows hydroponics with solid medium cultivation using an organic fertilizer, and has a potential to be applied to the fields of agriculture and horticulture. In particular, solid medium cultivation using rockwool is mainly performed in hydroponic cultivation of tomato. If the hydroponics employing an organic fertilizer could be applied to the hydroponic cultivation of tomato, it is expected to gain popularity in countries with high environmental consciousness such as Netherlands as well as in Japan. In particular, the scale of hydroponic cultivation of tomato in Netherlands exceeds 1000 ha. Thus, even when part of the hydroponic cultivation of tomato is replaced by the hydroponics employing an organic fertilizer, the market size is large.

Figure 1:
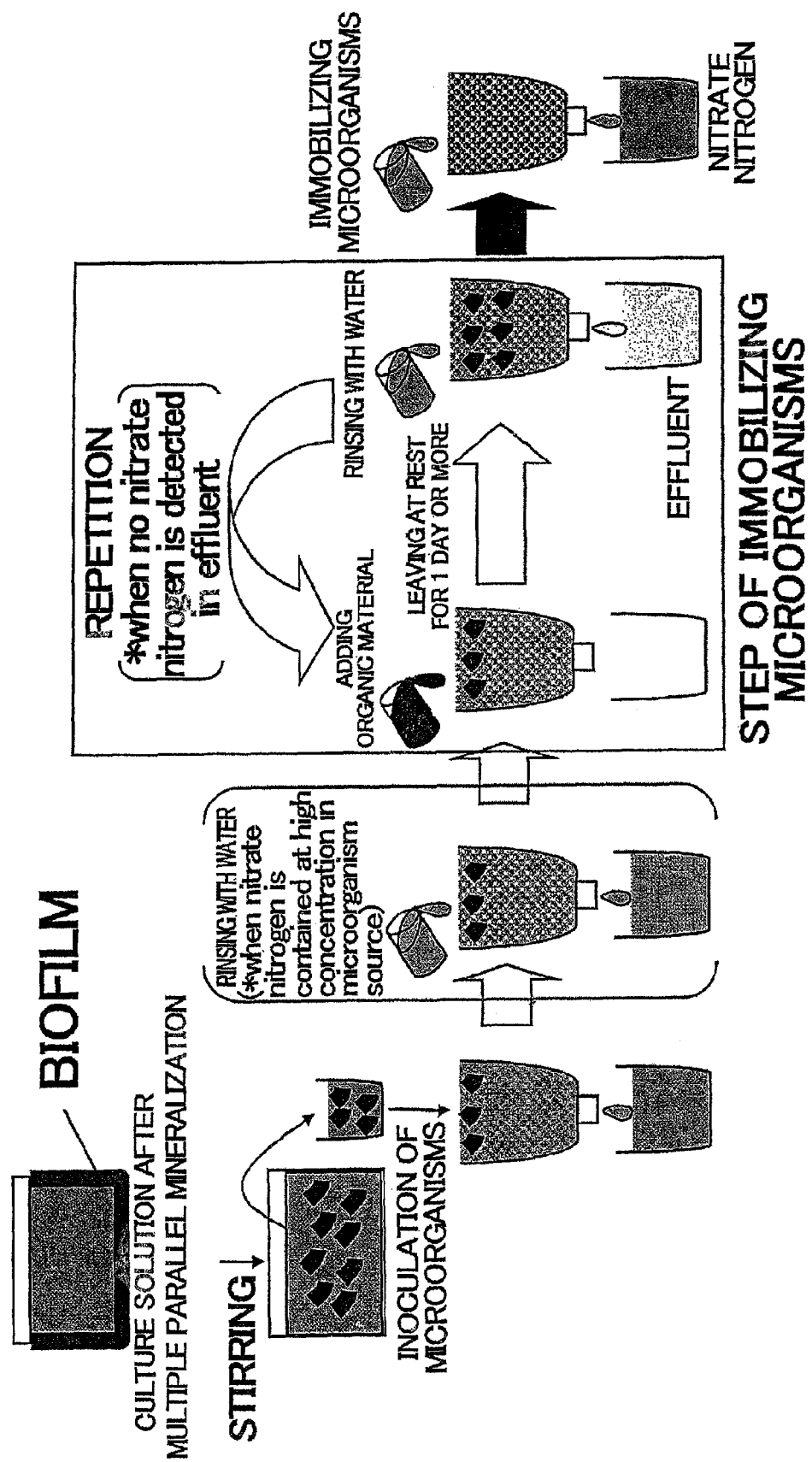
FIG. 1 is a diagram illustrating one aspect of a method involving immobilizing microorganisms on a carrier.
Figure 2:
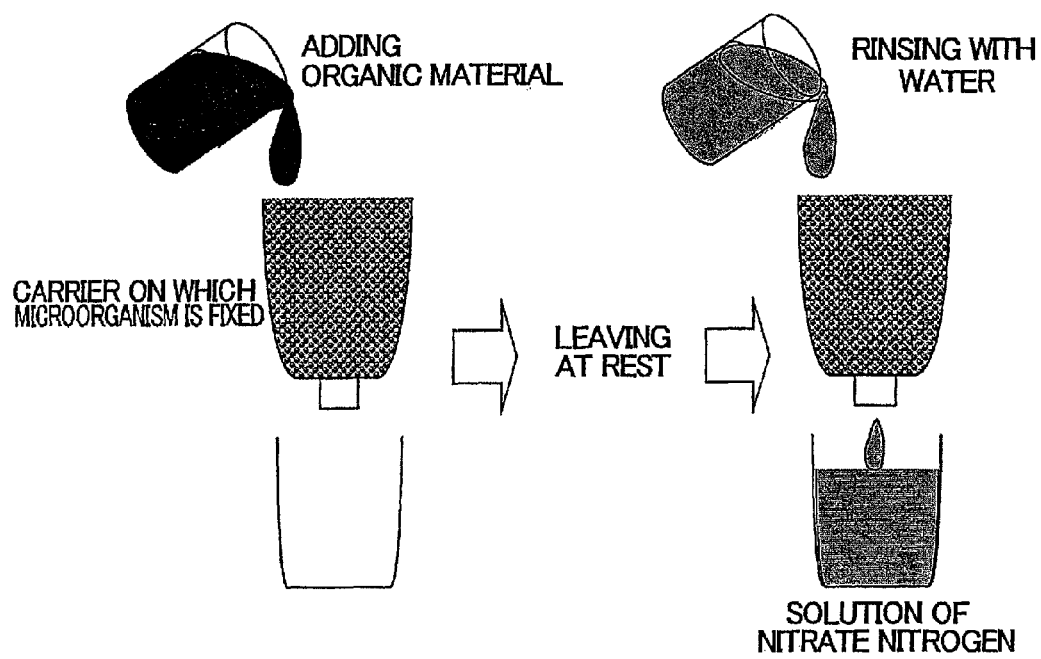
FIG. 2 is a diagram illustrating one aspect of a bioreactor optimized for a multiple parallel mineralization.
Figure 3A:
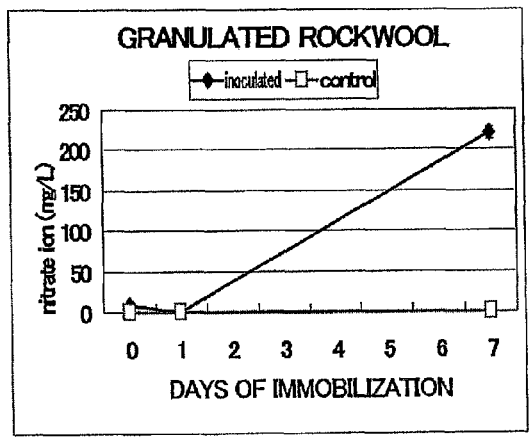
FIGS. 3(a) to 3(e) are graphs illustrating nitrate ion concentration in Example 1.
Figure 3B:
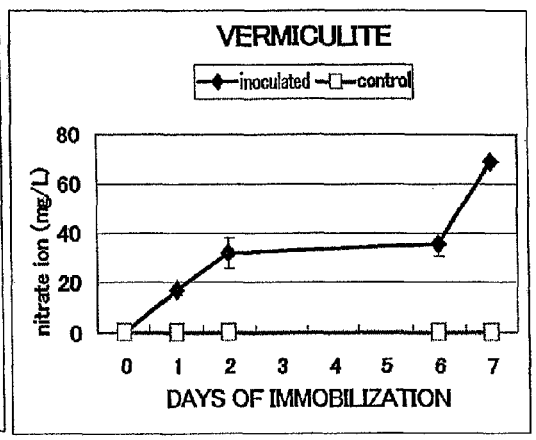
Figure 3C:
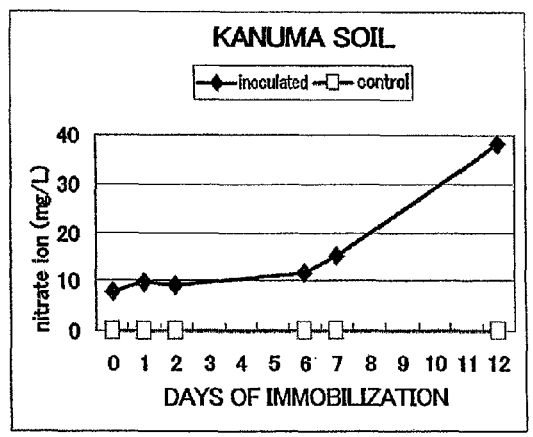
Figure 3D:
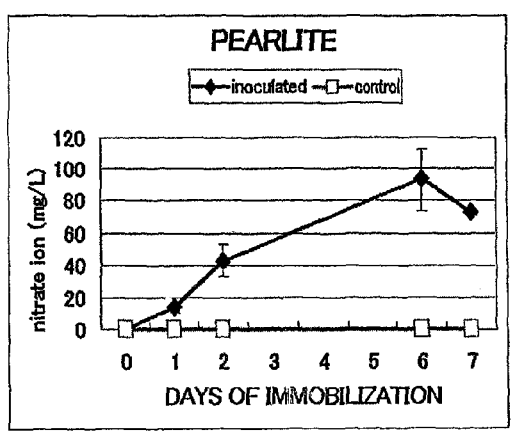
Figure 3E:
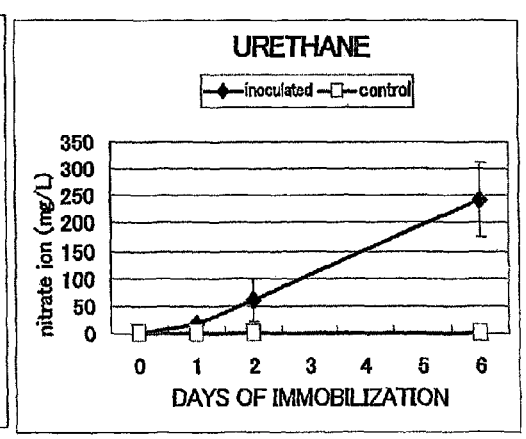
Figure 4:
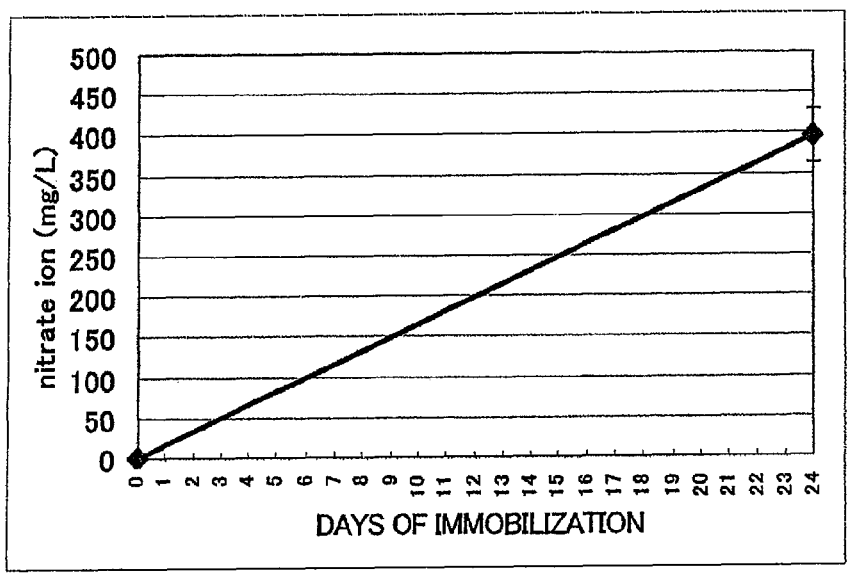
FIG. 4 is a graph illustrating nitrate ion concentration in Example 2.
Figure 5:
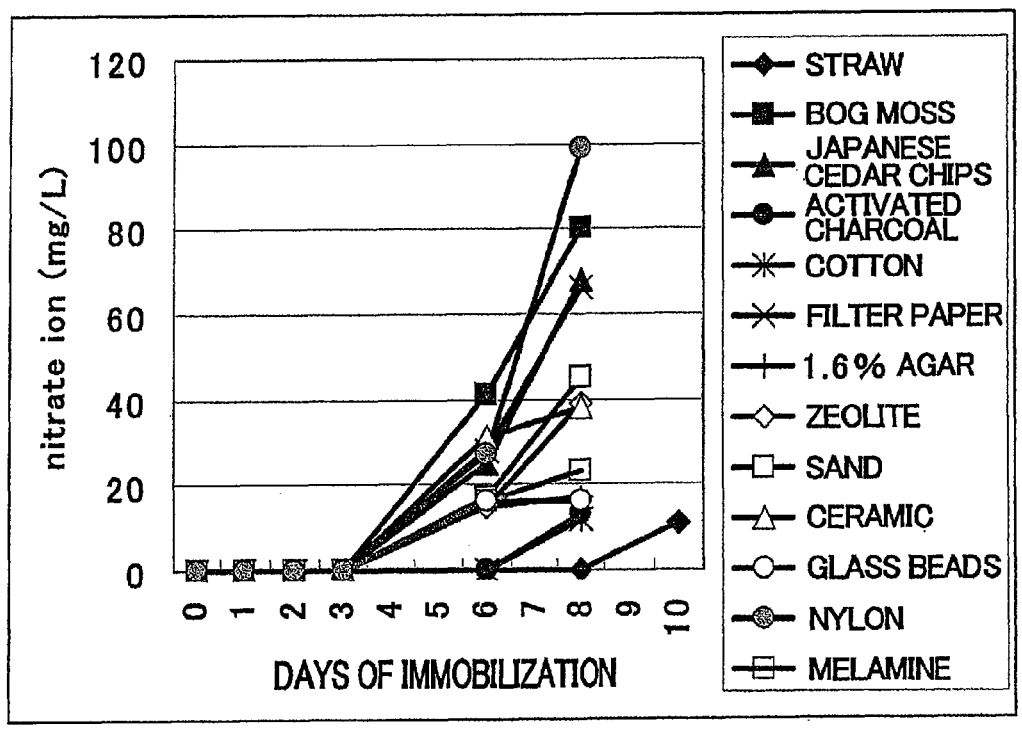
FIG. 5 is a graph illustrating nitrate ion concentration in Example 3.
Figure 6:
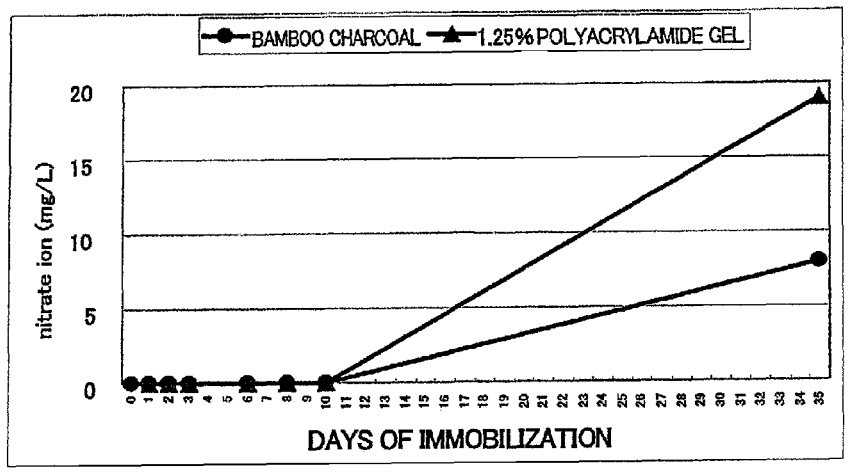
FIG. 6 is a graph illustrating nitrate ion concentration in Example 3.
Figure 7:
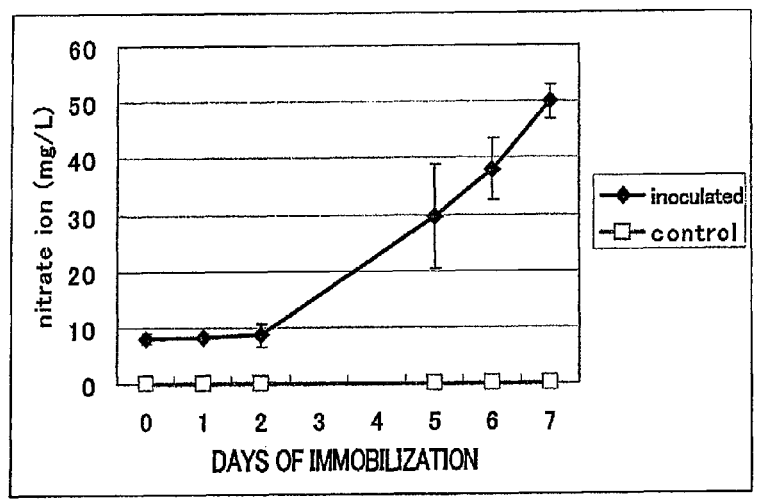
FIG. 7 is a graph illustrating nitrate ion concentration in the case of using rapeseed oil cake as an organic material in Example 4.
Figure 8:
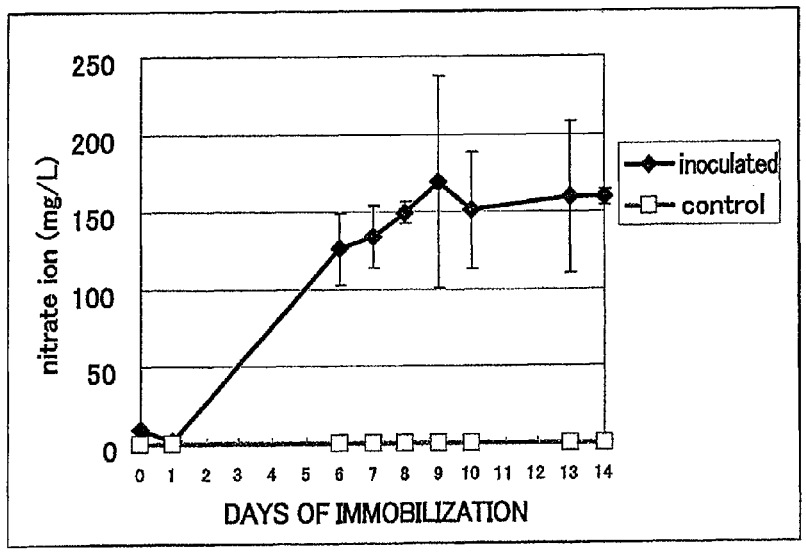
FIG. 8 is a graph illustrating nitrate ion concentration in the case of using corn steep liquor (CSL) as an organic material in Example 4.
Figure 9:
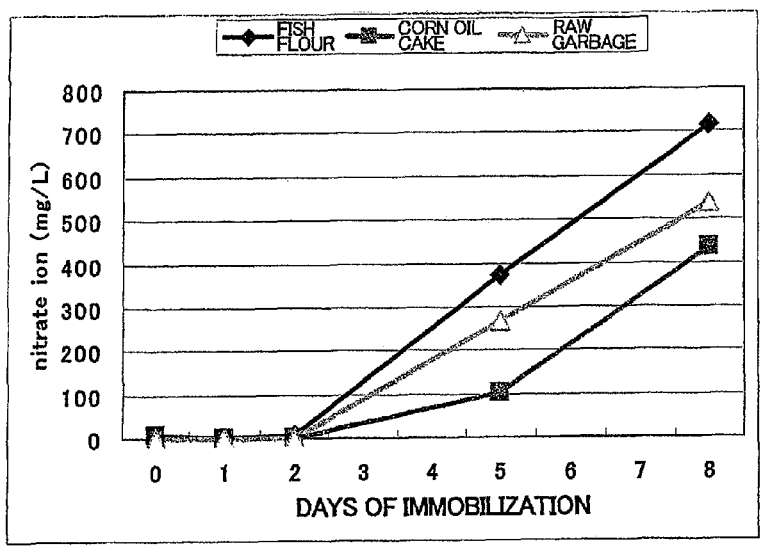
FIG. 9 is a graph illustrating nitrate ion concentration in Example 5.
Figure 10:
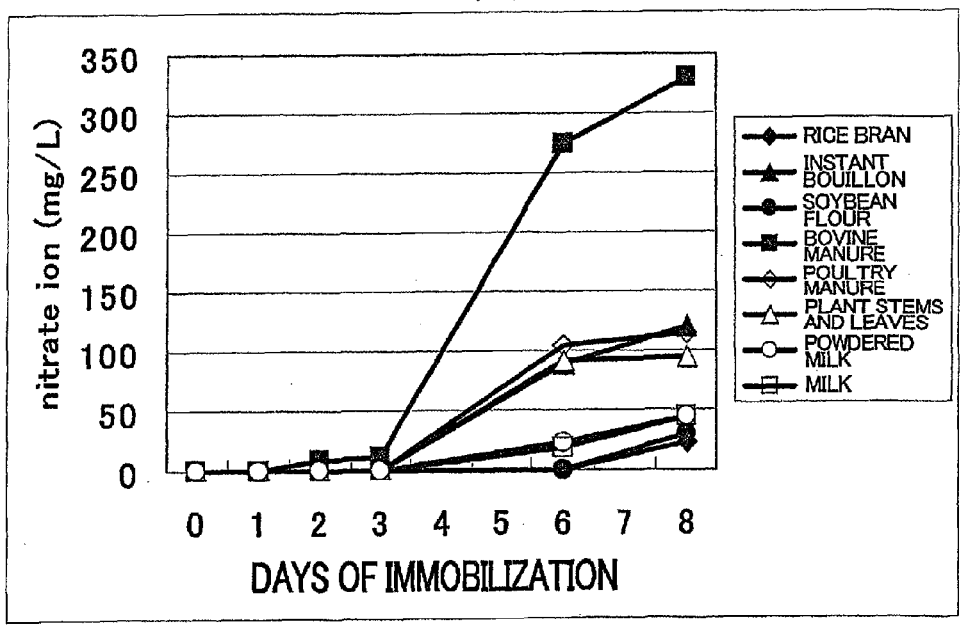
FIG. 10 is a graph illustrating nitrate ion concentration in Example 6.
Figure 11:
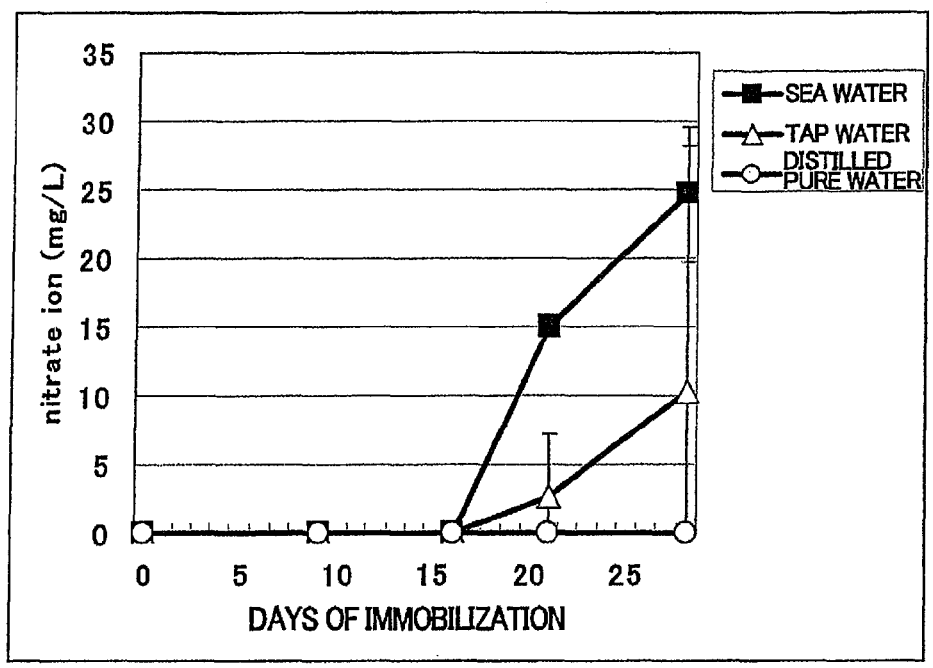
FIG. 11 is a graph illustrating nitrate ion concentration in the case of using sea water or tap water as a microorganism source in Example 7.
Figure 12:
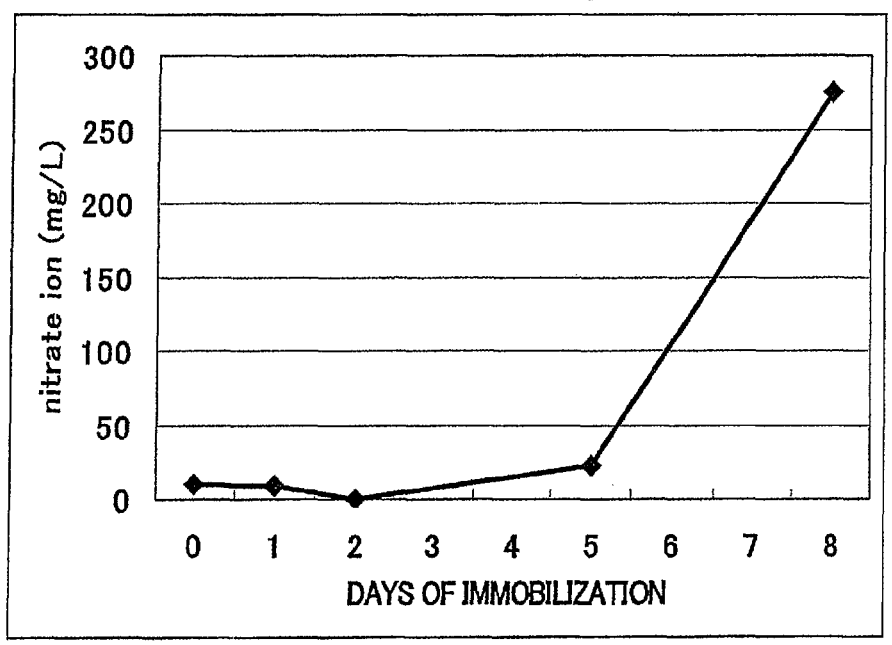
FIG. 12 is a graph illustrating nitrate ion concentration in the case of using soil as a microorganism source in Example 7.
Figure 13:
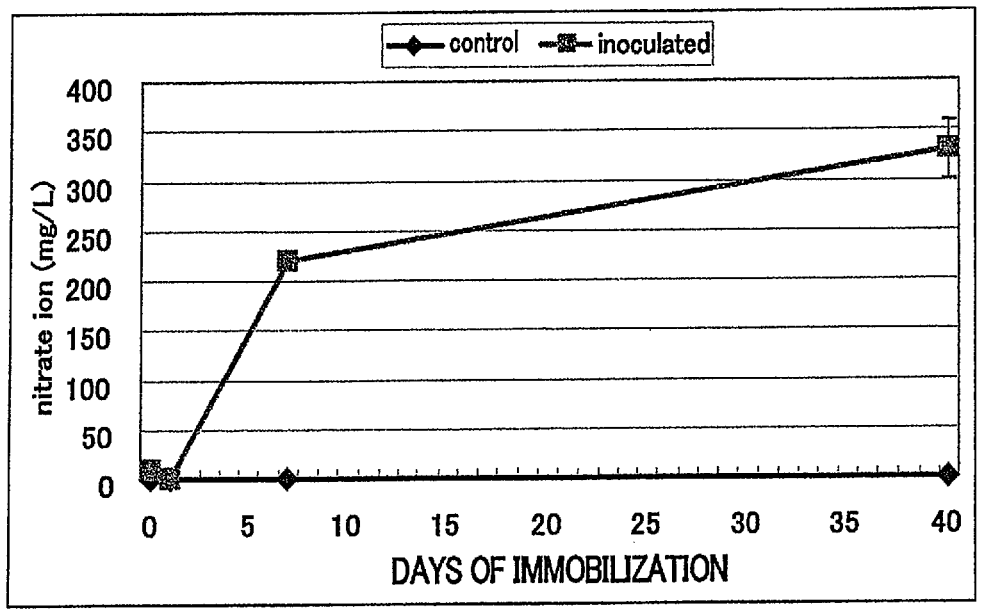
FIG. 13 is a graph illustrating nitrate ion concentration in Example 8.
Figure 14:
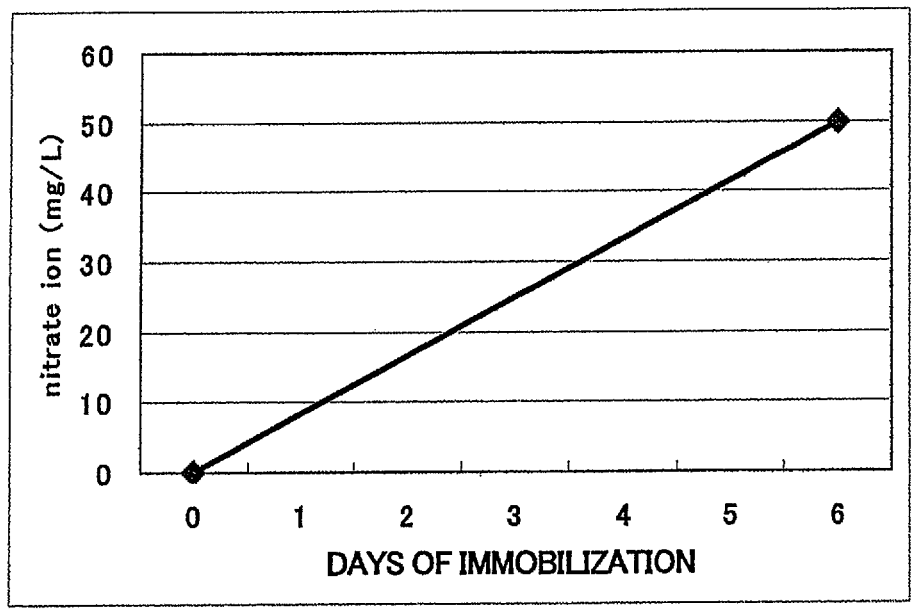
FIG. 14 is a graph illustrating nitrate ion concentration in Example 9.
Figure 15:
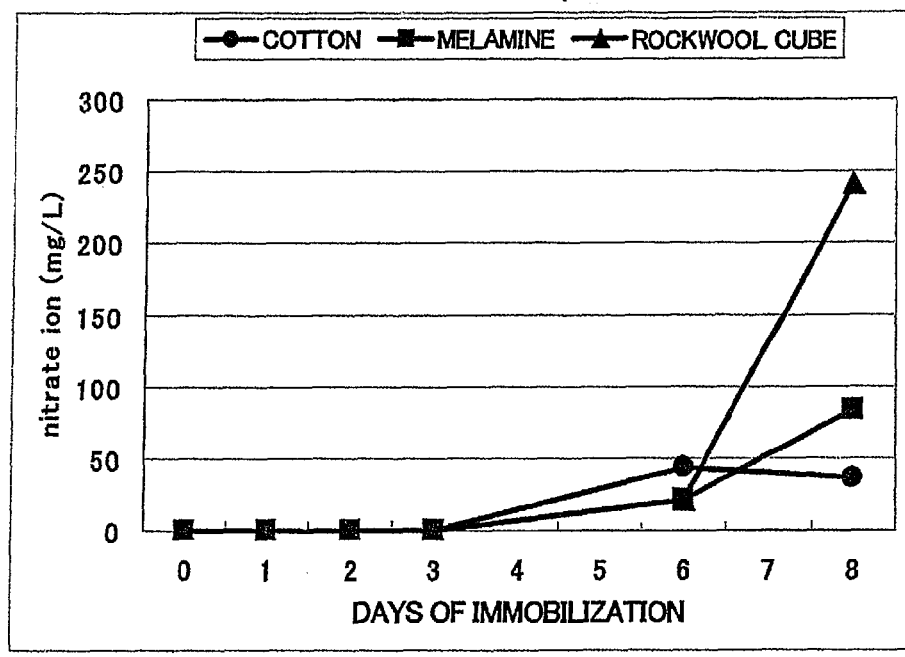
FIG. 15 is a graph illustrating nitrate ion concentration in Example 10.
Figure 16:
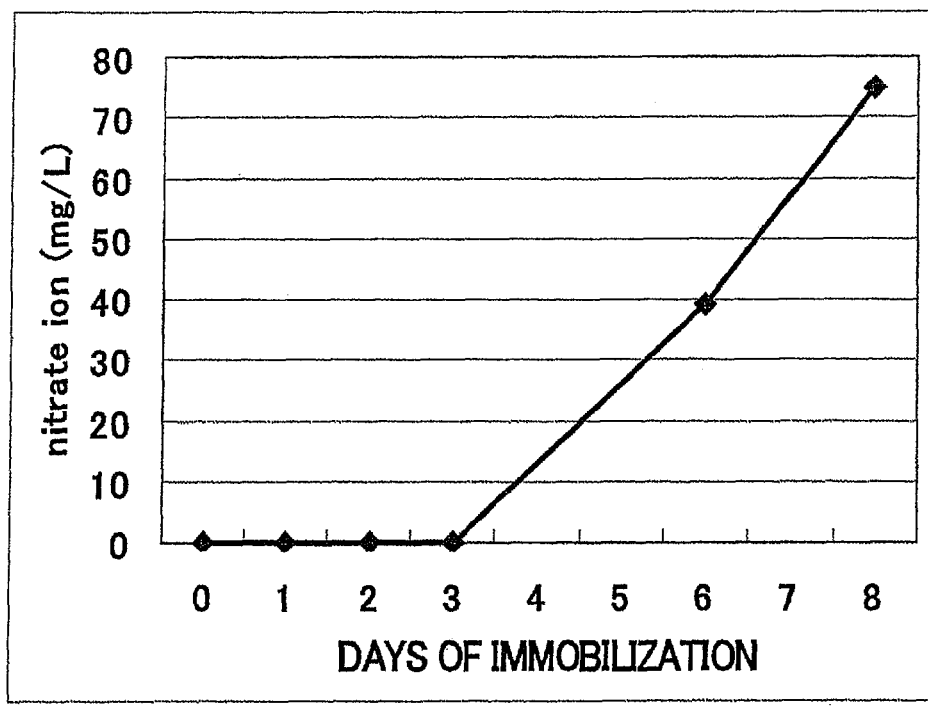
FIG. 16 is a graph illustrating nitrate ion concentration in Example 11.
Figure 17:
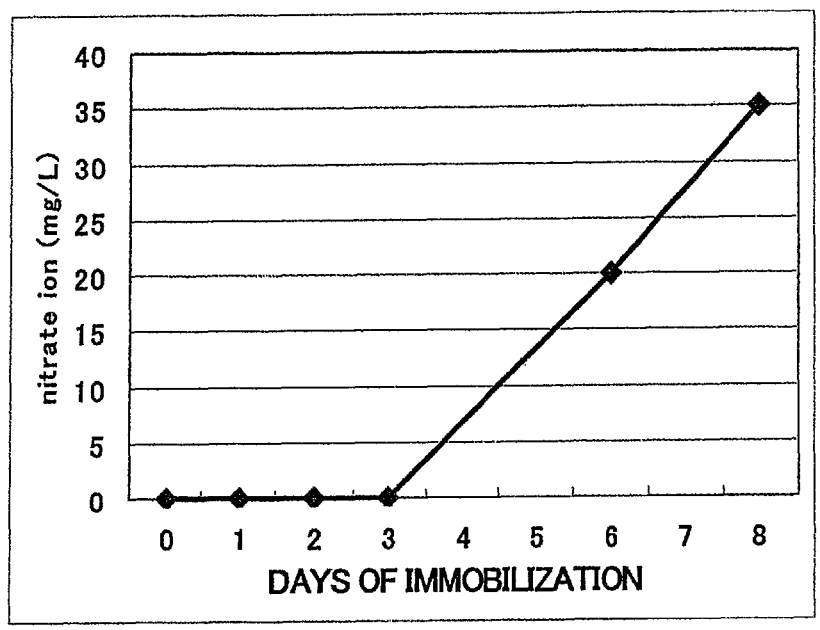
FIG. 17 is a graph illustrating nitrate ion concentration in Example 14.
Figure 18:
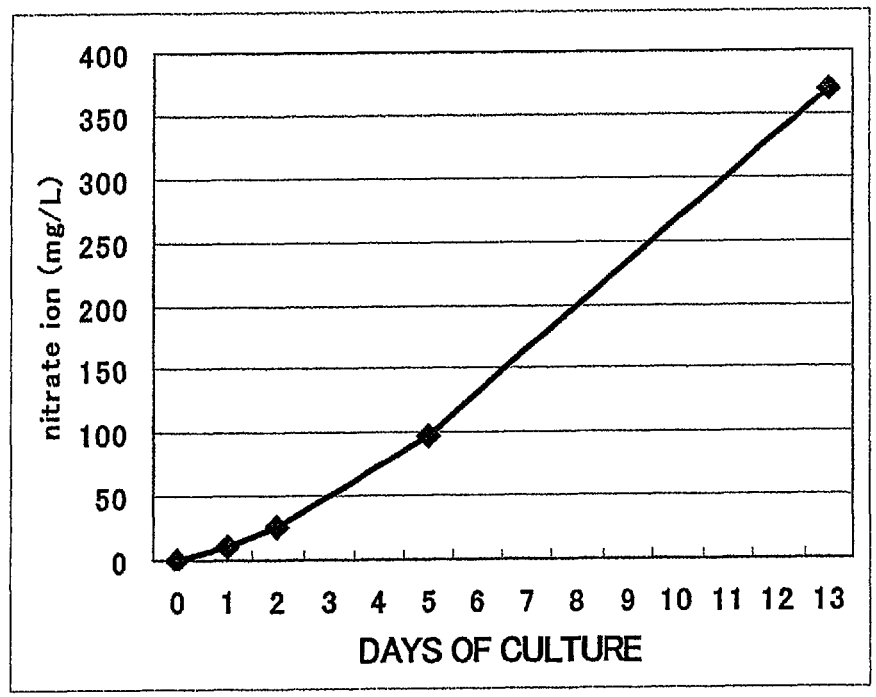
FIG. 18 is a graph illustrating nitrate ion concentration in Example 15.

The invention claimed is:

1. A method of manufacturing a column reactor for producing nitrate nitrogen as an inorganic nutrient from an organic material, the method comprising:
   (i) filling a container with a carrier (A) having ventilation, said carrier (A) comprising one or more porous carriers selected from the group consisting of rockwool, vermiculite, pearlite, zeolite, sand, glass, ceramic, urethane, nylon, a melamine resin, cedar chips, bog moss, filter paper and agar;
   (ii) adding thereto microorganisms capable of conducting a multiple parallel mineralization by mineralization of an organic material to produce nitrate nitrogen;
   (iii) subsequently adding an organic material (B) in an amount of 0.01 to 20 g, in terms of dry weight, with respect to 1 L of the carrier, said organic material (B) comprising one or more organic materials selected from the group consisting of a fish-based soluble fertilizer, fish flour, an oil cake, raw garbage, corn steep liquor, rice bran, soybean flour, a plant residue, milk, powdered milk and livestock manure; and
   (iv) then leaving the resultant material at rest until nitrate nitrogen starts to be produced in an effluent during a washing of the carrier by an addition of water to discharge the effluent from the carrier; thereby obtaining a carrier on which the microorganisms capable of conducting a multiple parallel mineralization are immobilized.

2. The method according to claim 1, wherein the container is equipped with a drain outlet, and the effluent is discharged from the drain outlet.

3. The method according to claim 1, the method comprising repeatedly performing treatments of adding the organic material, then leaving at rest, and washing the carrier through the addition of water to discharge an effluent from the carrier, before nitrate nitrogen starts to be produced in the effluent discharged during washing the carrier.

4. The method according to claim 1, wherein the microorganisms capable of conducting a multiple parallel mineralization is derived from one or more kinds of microorganism sources including microorganisms capable of conducting ammonification and microorganisms capable of conducting nitrification, the microorganism sources being selected from the group consisting of a culture solution obtained by culturing microorganisms capable of conducting a multiple parallel mineralization, dried microbial cells of the microorganisms obtained by drying the culture solution, the carrier on which microorganisms are immobilized, an effluent discharged from the carrier by adding water to the carrier on which microorganisms are immobilized, soil, tap water, water from lake and marsh, spring water, well water, river water, and sea water.

5. The method according to claim 1, wherein the organic material is a nitrogen-rich organic material having a content ratio of carbon to nitrogen, a C/N ratio, of 19 or less.

6. A method of manufacturing a column reactor capable of producing nitrate nitrogen as an inorganic nutrient from an organic material, the method comprising:
   (i) integrally molding a solid support (A) having gas permeability so as to maintain a solid shape, said solid support (A) comprising one or more porous carriers selected from the group consisting of rockwool, vermiculite, pearlite, zeolite, sand, glass, ceramic, urethane, nylon, a melamine resin, cedar chips, bog moss, filter paper and agar;
   (ii) adding thereto microorganisms capable of conducting a multiple parallel mineralization by mineralization of an organic material to produce nitrate nitrogen;
   (iii) subsequently adding an organic material (B) in an amount of 0.01 to 20 g, in terms of dry weight, with respect to 1 L of the carrier and then adding water, said organic material (B) comprising one or more organic materials selected from the group consisting of a fish-based soluble fertilizer, fish flour, an oil cake, raw garbage, corn steep liquor, rice bran, soybean flour, a plant residue, milk, powdered milk and livestock manure; and
   (iv) then leaving the resultant material at rest until nitrate nitrogen starts to be produced in an effluent during washing of the carrier by an addition of water to discharge the effluent from the carrier; thereby obtaining a carrier on which the microorganisms capable of conducting a multiple parallel mineralization are immobilized.

* * * * *